US012779127B2

(12) United States Patent
Blancke et al.

(10) Patent No.: US 12,779,127 B2
(45) Date of Patent: Nov. 3, 2026

(54) MECHANISM UNIT FOR A DRUG DELIVERY DEVICE AND DRUG DELIVERY DEVICE

(71) Applicant: Sanofi, Paris (FR)

(72) Inventors: Stefan Blancke, Frankfurt am Main (DE); Michael Jugl, Frankfurt am Main (DE)

(73) Assignee: SANOFI, Paris (FR)

( * ) Notice: Subject to any disclaimer, the term of this patent is extended or adjusted under 35 U.S.C. 154(b) by 965 days.

(21) Appl. No.: 17/920,157

(22) PCT Filed: Apr. 23, 2021

(86) PCT No.: PCT/EP2021/060628
§ 371 (c)(1),
(2) Date: Oct. 20, 2022

(87) PCT Pub. No.: WO2021/214272
PCT Pub. Date: Oct. 28, 2021

(65) Prior Publication Data

US 2023/0173188 A1 Jun. 8, 2023

(30) Foreign Application Priority Data

Apr. 23, 2020 (EP) .................................... 20315210

(51) Int. Cl.
*A61M 5/315* (2006.01)
*A61M 5/20* (2006.01)

(52) U.S. Cl.
CPC .......... *A61M 5/31541* (2013.01); *A61M 5/20* (2013.01); *A61M 5/31551* (2013.01);
(Continued)

(58) Field of Classification Search
CPC ................ A61M 5/31541; A61M 5/20; A61M 5/31551; A61M 5/31585; A61M 5/31568; A61M 2207/10
See application file for complete search history.

(56) References Cited

U.S. PATENT DOCUMENTS

2009/0247951 A1* 10/2009 Kohlbrenner ..... A61M 5/31553 604/134
2013/0310762 A1 11/2013 Smith et al.
(Continued)

FOREIGN PATENT DOCUMENTS

CN 101594896 A 12/2009
CN 108025138 A 5/2018
(Continued)

OTHER PUBLICATIONS

International Preliminary Report on Patentability in International Appln. No. PCT/EP2021/060628, mailed on Nov. 3, 2022, 9 pages.
(Continued)

*Primary Examiner* — Tasnim Mehjabin Ahmed
(74) *Attorney, Agent, or Firm* — Bond, Schoeneck & King, PLLC

(57) ABSTRACT

A mechanism unit for a drug delivery device, comprising a housing, a piston rod, and a dose setting and drive mechanism that comprises a first drive member, a second drive member, and a clutch mechanism, which has at least two different states: a setting state and a delivery state. In the setting state, the second drive member is rotationally secured with respect to the housing at least against rotation in a delivery direction, and, in the delivery state, the second drive member is rotatable relative to the housing in the delivery direction. In the setting state, the first drive member is rotatable relative to the second drive member at least in the delivery direction. In the delivery state, the second drive member is rotationally locked to the first drive member at
(Continued)

least against rotation of the second drive member relative to the first drive member in the delivery direction.

19 Claims, 10 Drawing Sheets

(52) U.S. Cl.
CPC ..... *A61M 5/31585* (2013.01); *A61M 5/31568* (2013.01); *A61M 2207/10* (2013.01)

(56) References Cited

U.S. PATENT DOCUMENTS

| | | | |
|---|---|---|---|
| 2017/0304554 | A1 | 10/2017 | Morris |
| 2019/0217014 | A1 | 7/2019 | Davies et al. |

FOREIGN PATENT DOCUMENTS

| | | | |
|---|---|---|---|
| DE | 102005060929 A1 | | 3/2007 |
| EP | 3067081 A1 | | 9/2016 |
| WO | WO 2008/031235 | | 3/2008 |
| WO | 2012130705 | A1 | 10/2012 |
| WO | 2014033195 | A1 | 3/2014 |
| WO | 2016055631 | A1 | 4/2016 |

OTHER PUBLICATIONS

International Search Report and Written Opinion in International Appln. No. PCT/EP2021/060628, mailed on May 10, 2021, 10 pages.
First Office Action for Chinese Patent Application No. 2021800299172 issued Oct. 31, 2024 (13 pages total, 6 in English).
Search Report for Chinese Patent Application No. 2021800299172 dated Oct. 29, 2024 (2 pages in English).
Search Report for Chinese Patent Application No. 202180029917.2 dated May 14, 2025 (2 pages in English).

* cited by examiner

MECHANISM UNIT FOR A DRUG DELIVERY DEVICE AND DRUG DELIVERY DEVICE

CROSS-REFERENCE TO RELATED APPLICATIONS

The present application is the national stage entry of International Patent Application No. PCT/EP2021/060628, filed on Apr. 23, 2021, and claims priority to Application No. EP 20315210.3, filed on Apr. 23, 2020, the disclosures of which are incorporated herein by reference.

TECHNICAL FIELD

The present disclosure relates to a mechanism unit for a drug delivery device. The present disclosure further relates to a drug delivery device comprising the mechanism unit and to a method of producing the drug delivery device.

BACKGROUND

In drug delivery devices, especially in the case of drug delivery devices which are operated by medically untrained patients, it is important that the size of the dose delivered by the drug delivery device does correspond to the size which was set by the user as consistently as possible while the device is in use to dispense drug from a cartridge or reservoir. Drug delivery devices often use piston rods which are moved by a drive mechanism of the device and are arranged to drive a bung within a reservoir body of a reservoir retaining a drug distally relative to the reservoir body in order to dispense the drug from the reservoir. During manufacturing of drug delivery devices the distances between a distal end of the piston rod and a proximal end of the bung which face one another may vary widely after the initial assembly of the device. From a manufacturing perspective it may be possible to position the piston rod relative to a housing of the drive mechanism of the drug delivery device pretty accurately. However, it is usually difficult to ensure that the position of the bung relative to the reservoir body is as precisely set for reservoirs having the nominally same liquid filling levels, e.g. due to the deformable materials usually used for the bungs. Thus, the initial positions of the bung relative to the reservoir body may vary. Variations in the reservoir body dimensions may have a similar effect, although the influence of the bung may be more pronounced. The mentioned variations increase the variations in the distances between the distal end of the piston rod and the proximal end of the bung in different devices after the devices have been assembled. Therefore, an initial target distance between the piston rod and the bung, which should be achieved during the assembling process of the device, has to be chosen to be great enough to take account of a wide range of possible bung positions relative to the reservoir body in order to avoid that during assembling of the device the piston rod already exerts pressure on the bung which is undesirable, e.g. as it puts mechanical pre-load on the bung. Thus, the fluctuations in the bung position often require that a comparatively large initial target distance is chosen.

A defined initial position between the bung and the piston rod for a variety of devices may be achieved by measures which allow a connection between the drive mechanism and the reservoir or the reservoir unit which is variable, i.e. it does not rely on fixing elements which have defined positions on the respective unit, reservoir unit and drive mechanism unit. Connection methods which allow a variable connection are an adhesive connection or a welded connection, for example. However, if a more reliable connection should be used such as one which is established by means of rigid fixing features or securing features, e.g. for a form-fit connection, the relative position after assembling of the device between the bung and the piston rod still varies on account of the variations in the reservoir unit, sometimes considerably.

In order to achieve a defined position between the piston rod and the bung before the first dose is administered to a patient sometimes so-called priming steps are used, where the user has to perform a dose setting and delivery step before the first (self-) administration of the drug takes place. Such a procedure is often termed “air shot”. This procedure, however, is still not satisfactory, as it is not sure whether the user—although instructed to do so—indeed performs that step.

Moreover, if the concentration of drug within the reservoir is increased it may even occur that the initial distance between the piston rod and the bung is so great that it is greater than a regular dose—e.g. greater than the minimum settable dose or even a greater dose-which is dispensed by the drug delivery device or even greater than the maximum settable dose which can be dispensed in one dispensing operation by the drug delivery device. Thus, the first dose which is set to be dispensed may be completely absorbed by the initial gap between the piston rod and the bung which has to be closed, before drug can be dispensed via the bung being displaced relative to the reservoir body. This, of course, is very problematic. Moreover, the second dose may still not be dispensed accurately, even if a priming dose has been dispensed as there may still be a substantial gap after the first dose has been dispensed.

An option to achieve a defined initial position is to activate the drive mechanism by setting a dose and dispensing the set dose after the device has been assembled until the piston rod has reached the desired position, expediently before the device is even provided to the user. However, drug delivery devices, especially the ones configured to dispense a variable, e.g. user-settable, dose, often comprise a mechanism which tracks the (end of) content of the reservoir or the maximum amount which can be dispensed from the reservoir. This mechanism is dimensioned such that it is ensured that there is still some drug left in the reservoir when the last dose has been dispensed, i.e. the reservoir is overfilled. This, of course, takes care of avoiding the risk of underdosing. The tracking mechanism for tracking the (end of) content of the reservoir usually has a tracking member which is moved relative to a guide track towards an end position when the dose is set but is not moved relative to the guide track when the set dose is delivered. When the tracking member reaches the end position, the reservoir is considered empty. In the end position, (further) increasing the set dose may be prevented by the tracking member.

Usually, drug delivery devices dispense doses in amounts which are whole-number multiples of a unit increment. As the tracking member also moves during the first setting and dispensing of the dose which may be performed to eliminate the initial gap between the piston rod and the bung as described previously, this results in that the reservoir has to be overfilled with drug at least to an amount which corresponds to the maximum initial distance between the piston rod and the bung when assembling a variety of devices of nominally identical construction. Thus, this overfilled drug is lost, as it is usually not dispensed. The amount of drug which has to be overfilled may be even greater than the maximum dose which can be set with the device as has been explained above.

SUMMARY

This disclosure provides improved drug delivery device(s) and/or improved method(s) for producing a drug delivery device.

In an embodiment there is provided a mechanism unit for a drug delivery device, the mechanism unit comprising: a housing having a proximal end and a distal end, a piston rod, the piston rod being movable relative to the housing, e.g. movably retained in the housing, a dose setting and drive mechanism which is configured to perform a dose setting operation for setting a dose to be delivered and a dose delivery operation for delivering the set dose by transferring a delivery force to the piston rod in order to drive the piston rod in a distal direction relative to the housing in the dose delivery operation, the dose setting and drive mechanism comprising a first drive member which is in mechanical cooperation with the piston rod to transfer the delivery force to the piston rod, the first drive member being axially secured and rotatable relative to the housing, wherein rotation of the first drive member in a delivery direction relative to the housing results in movement of the piston rod in the distal direction and rotation in the direction opposite to the delivery direction results in proximal movement of the piston rod, a second drive member which is arranged to be mechanically coupled to the first drive member to transfer the delivery force to the first drive member, wherein the dose setting and drive mechanism comprises a clutch mechanism which has at least two different states, a setting state and a delivery state, wherein, in the setting state, the second drive member is rotationally secured with respect to the housing at least against rotation in the delivery direction, and wherein, in the delivery state, the second drive member is rotatable relative to the housing in the delivery direction, wherein, in the setting state, the first drive member is rotatable relative to the second drive member and the housing at least in the delivery direction, and wherein, in the delivery state, the second drive member is rotationally locked to the first drive member at least against rotation of the second drive member relative to the first drive member in the delivery direction.

Since the first drive member is rotatable in the setting state in the delivery direction relative to the second drive member, the piston rod can be moved in the distal direction, e.g. before the final assembly of the drug delivery device takes place. This is preferably done by the direct manual or automatic rotation of the first drive member, for example by an auxiliary tool. This rotation allows the piston rod to move in the distal direction until a desired distance between the proximal end of a bung in a reservoir of the reservoir unit and the distal end of the piston rod is reached, when the device is assembled, e.g. by connecting the mechanism unit and the reservoir unit. This makes it possible to precisely adjust the desired distance between the bung and the piston rod prior to the first delivery of a dose and the first operation of the drive mechanism, regardless of the bung position, the size or original fill level of the reservoir. In this way, one or more air shots can be avoided before the drug is administered to a patient using the drug delivery device. This not only means that there is no waste of the medication, but also that the user-friendliness and thus the safety of the drug delivery device after assembly is significantly improved.

In an embodiment the mechanism unit is configured to be connected to a reservoir unit for assembling the two units for a drug delivery device.

This allows the piston rod position to be adjusted before the drug delivery device is assembled into the operational state in which state it may reach the patient or customer. This can be particularly advantageous if the mechanism unit is used for differently designed reservoir units, which for example may have different positions of the bung.

In an embodiment the first drive member is accessible from the exterior of the housing for manipulations such that, in the setting state, the position of the piston rod relative to the housing is adjustably by rotation of the first drive member, preferably before or after the mechanism unit and the reservoir unit are connected.

The accessibility of the first drive member from the exterior of the housing allows the piston rod to be adjusted when the mechanism unit is already assembled, but the drug delivery device is not yet fully assembled.

In an embodiment the first drive member is accessible from the distal end of the housing for manipulations. Then, in the setting state, the position of the piston rod relative to the housing may be adjusted by rotation of the first drive member. This may be done before the mechanism unit and the reservoir unit are connected.

In an embodiment the first drive member is accessible from the proximal end of the housing for manipulations. Then, in the setting state, the position of the piston rod relative to the housing may be adjusted by rotation of the first drive member. This may be done before or after the mechanism unit and the reservoir unit are connected.

The accessibility of the first drive member from the proximal end of the housing allows the piston rod to be adjusted before the drug delivery device is fully assembled and before or after the mechanism unit and the reservoir unit are connected. An opening through which the first drive member is accessible may be closed by a closing component, e.g. a button component, which provides a user interface for the drug delivery device.

In an embodiment the second drive member is axially movable relative to the first drive member and the housing, e.g. in the distal direction, for switching between the setting state and the delivery state. Preferably, distal movement of the second drive member relative to the first drive member and the housing from an initial position in the setting state causes the mechanism unit to transition to the delivery state, wherein proximal movement of the second drive member relative to the first drive member and the housing in the delivery state causes the mechanism unit to transition to the setting state.

In an embodiment the first drive member is engaged to the piston rod. The piston rod may be engaged to the housing. Preferably, the first drive member is directly engaged with the piston rod.

This allows a movement of the first drive member relative to the housing to have a direct effect on the axial position of the piston rod relative to the housing.

In an embodiment the first drive member is threadedly engaged to the piston rod. The piston rod may be splined to the housing.

In an embodiment the first drive member is rotatable relative to the piston rod, preferably in the delivery state and/or the setting state.

The threaded engagement of the first drive member with the piston rod causes a rotary movement of the first drive member to cause an axial displacement of the piston rod.

This enables the piston rod to be moved into a desired position relative to the housing.

In an embodiment the first drive member is splined to the piston rod. The piston rod may be threadedly engaged to the housing.

In an embodiment the first drive member is rotationally constrained with respect to the piston rod in the delivery direction and the direction opposite to the delivery direction, preferably in the delivery state and/or the setting state.

This allows a movement of the first drive member to have a direct effect on the axial position of the piston rod relative to the housing.

In an embodiment the first drive member is secured against proximal and distal movement relative to the housing, preferably in the delivery state and/or the setting state.

In an embodiment the first drive member and/or the second drive member is a sleeve.

In an embodiment the piston rod extends through the first drive member and/or the second drive member.

In an embodiment the first drive member comprises a first locking feature and the second drive member comprises a second locking feature. The first and second locking features may be configured to interact so as to rotationally lock the first drive member and the second drive member against relative rotation in at least one direction and/or two directions. Preferably, when the first and second locking features interact mechanically, e.g. engage one another, the second drive member cannot be rotated relative to the first drive member at least in the delivery direction.

In an embodiment the first locking feature is rotationally and axially immovable relative to the first drive member. The second locking feature may be rotationally and axially immovable relative to the second drive member.

In an embodiment the first locking feature is engaged with the second locking feature in the delivery state.

In an embodiment the first locking feature and the second locking feature are disengaged in the setting state.

In an embodiment the first locking feature and the second locking feature are disengaged in the setting state and the first locking feature is rotatable relative to the second locking feature in the setting state.

In an embodiment the first locking feature is engaged with the second locking feature in the setting state.

In an embodiment the first locking feature and the second locking feature are configured, such that the first locking feature may be rotatable relative to the second locking feature in the delivery direction and rotationally secured with respect to the second locking feature in the direction opposite to the delivery direction, if the first locking feature is engaged with the second locking feature. This implies that the second drive member cannot be rotated relative to the first drive member in the delivery direction.

In an embodiment the first locking feature and the second locking feature are designed such that when the first locking feature is engaged with the second locking feature, the first drive member may occupy one of several stable positions relative to the second drive member, wherein the angular distance between the stable positions may be adjusted to, e.g. corresponds to, the angle the user has to rotate a dose setting member to set the smallest dose which can be delivered by the drug delivery device. This dose may correspond to one unit increment.

In an embodiment the first locking feature and the second locking feature are designed such that the distance between the stable positions is such that a movement of the first drive member relative to the second drive member from one of the stable positions to the next immediately adjacent stable position would result at most in an axial movement of the piston rod corresponding to the axial movement of the piston rod during the delivery of a dose of one unit increment.

In an embodiment the first locking feature and the second locking feature are designed as mating ratchet teeth.

In an embodiment the dose setting and drive mechanism comprise a dose setting member which is moveable relative to the housing in the setting state from an initial position to a dose set position in order to set a dose of drug, particularly when the device has been fully assembled.

In an embodiment the dose setting member is rotationally constrained with respect to the second drive member in the delivery state and rotatable relative to the second drive member in the setting state.

In an embodiment the first drive member is rotationally constrained to the dose setting member and the second drive member in the delivery state in the direction opposite to the delivery direction. Moreover, the first drive member may be rotatable relative to the dose setting member and the second drive member in the delivery state in the delivery direction.

In an embodiment the first drive member is rotatable relative to the dose setting member and the second drive member in the setting state in the delivery direction. Furthermore, the first drive member may be rotatable relative to the dose setting member and the second drive member in the setting state in the delivery direction and in the direction opposite to the delivery direction.

In an embodiment the mechanism unit comprises an energy storage. The energy storage may be configured such that in the setting state energy is stored in the energy storage due to a movement of a setting member, preferably the dose setting member, by a user. The energy storage may be configured such that in the delivery state the stored energy of the energy storage is released to support the delivery process. The energy storage may be a drive spring.

In an embodiment, a drug delivery device is provided, which comprises the mechanism unit, preferably as described further above.

In an embodiment the drug delivery device comprises a reservoir unit, wherein the reservoir unit comprises or is provided to retain a reservoir holding a drug.

In an embodiment, the reservoir is a cartridge.

In an embodiment the drug delivery device is an injection device, e.g. a needle based injection device, preferably a pen-type injector.

In an embodiment, a method of producing a drug delivery device is provided which comprises the following steps:

a) providing a reservoir unit, the reservoir unit comprising a reservoir containing a drug, wherein a bung is movably retained in the reservoir, the reservoir being retained in a reservoir unit body,
b) providing the mechanism unit described above,
c) determining a bung position of the bung relative to the reservoir unit body,
d) determining, based on the determined bung position, a desired piston rod position of the piston rod relative to the housing where the desired piston rod position is determined such that, if the mechanism unit and the reservoir unit are connected, the piston rod and the bung are arranged at a predetermined distance relative to one another, and determining a particular displacement distance by which the piston rod has to be displaced relative to the housing in the distal direction to be in the desired piston rod position,
e) in the setting state of the mechanism unit, rotating the first drive member relative to the second drive member to displace the piston rod relative to the housing by the particular displacement distance, and f) after or before step e), connecting the reservoir unit and the mechanism unit to one another.

Consequently, the rotation of the first drive member allows the exact positioning of the distal end of the piston rod relative to the proximal end of the bung. Therefore, the size of the first dose delivered by the drug delivery device does precisely correspond to the size which was set by the user. Thus, neither air shots are necessary nor is there a danger that the patient will receive a wrong dose.

These and other aspects, advantages and expediencies will become apparent from the embodiments described hereinafter.

BRIEF DESCRIPTION OF THE FIGURES

Embodiments will now be described, by way of example only, with reference to the accompanying drawings, in which.

DETAILED DESCRIPTION

Figure 1:
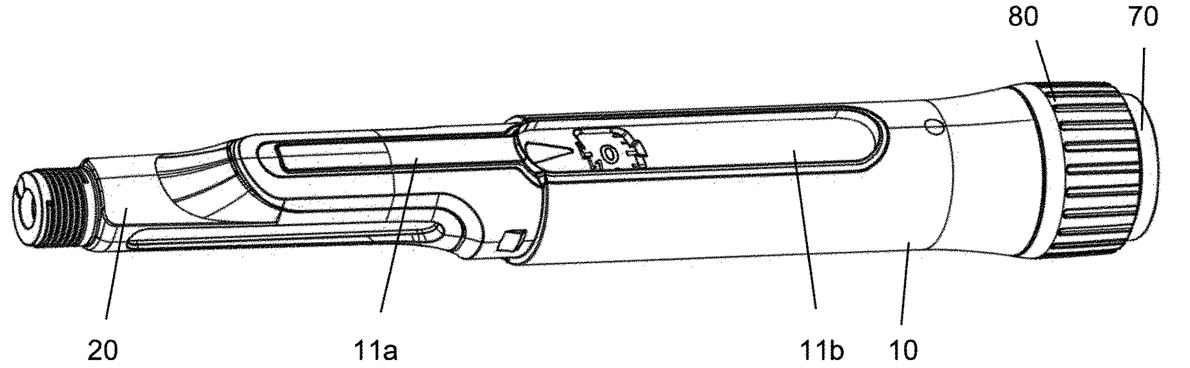
FIG. 1 shows a top view of a drug delivery device according to a first embodiment of the present disclosure.
Figure 2:
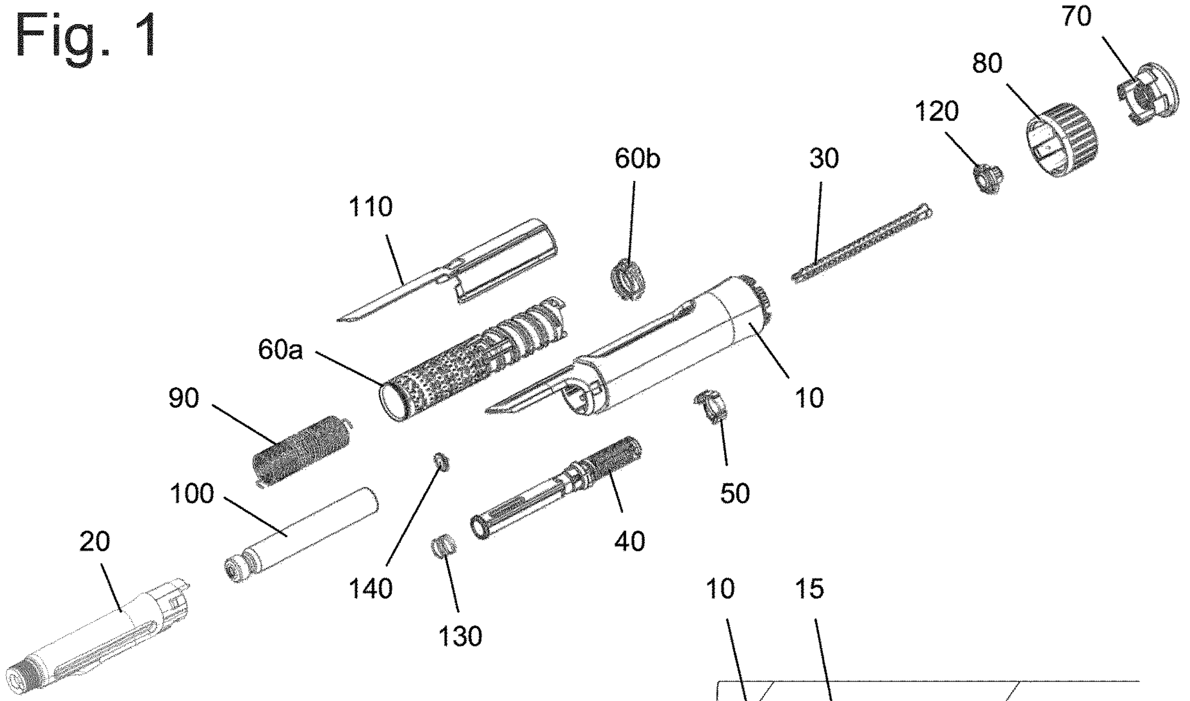
FIG. 2 shows an exploded view of the components of the device of FIG. 1.

FIG. 1 shows a drug delivery device in the form of an injection pen. The device has a distal end (left end in FIG. 1) and a proximal end (right end in FIG. 1). The component parts of the drug delivery device are shown in FIG. 2. The drug delivery device comprises a body or housing 10, a reservoir unit body (or cartridge holder) 20, a piston rod (or lead screw) 30, a drive member (or drive sleeve) 40, a nut 50, a dose setting member (or dose indicator or number sleeve or scale drum) 60, a button 70, a dial grip or dose selector 80, a torsion spring 90, a reservoir (or cartridge) 100, a gauge element 110, a clutch plate 120, a clutch spring 130 and a bearing 140. A needle arrangement (not shown) with a needle hub and a needle cover may be provided as additional components, which can be exchanged as explained above. All components are located concentrically about a common principal axis I (FIG. 3*b*) of the mechanism.

The housing 10 or body is a generally tubular casing element having a proximal end with an enlarged diameter. The housing 10 provides location for the liquid medication reservoir 100 and reservoir unit body 20. As shown in FIGS. 1 and 2, the housing comprises a first window 11*a* and a second window (or lens) 11*b* which are incorporated into the housing body e.g. by twin-shot molding. The windows 11*a*, 11*b* may be molded during a first shot in a translucent (and preferably transparent) material, and the outer cover of the housing is molded during a second shot in an opaque material.

In the embodiment of FIGS. 1 to 3*b* the housing comprises an insert 12 as an integral part located as an inner wall near the distal end of the housing. The insert 12 may be moulded in the translucent material. As an alternative, the insert or parts thereof may be formed in the opaque material or as a separate component part as depicted in the embodiment of FIG. 4.

The insert 12 is a cup-shaped component part with a sidewall 13 and a tube 14 extending through the insert 12, thus forming an annular space there between. Arms 15 extend radially outwards from the sidewall 13. A bottom wall 16 connects the sidewall 13 and the tube 14 on the distal side of the insert 12, whereas the opposite proximal side is open. The insert 12 has various interfaces. For example, the tube 14 of insert 12 comprises an inner thread 17 engaging the piston rod 30. In addition the radial space between the tube 14 and the outer sidewall 13 may provide a bearing area receiving the drive spring 90 and the clutch spring 130. Further, spline teeth 18 are provided on the insert 12 engaging corresponding spline teeth 41 at the distal end of drive member 40. Teeth 18 interact with drive member 40 to rotationally couple and de-couple the drive member and the housing 10.

Figure 4:
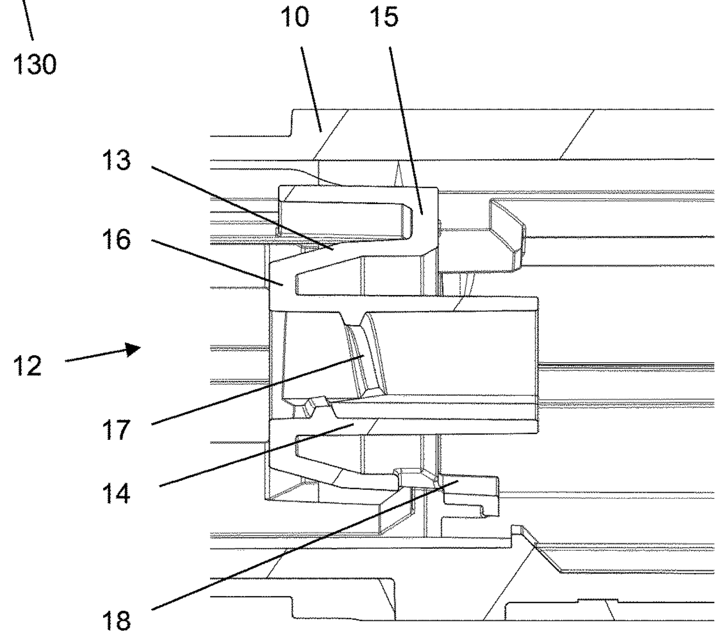
FIG. 4 shows in a sectional view a detail of a device according to a second embodiment of the present disclosure.

In the embodiment of FIG. 4, the insert is an integral part of an inner housing shell which inner shell is partially surrounded by an external housing shell. The shells may be formed by two consecutive shots of injection moulding such that the shells are permanently attached to each other. For example, the inner shell is formed from a transparent or translucent material, whereas the outer shell is formed from an opaque material.

Figure 5A:
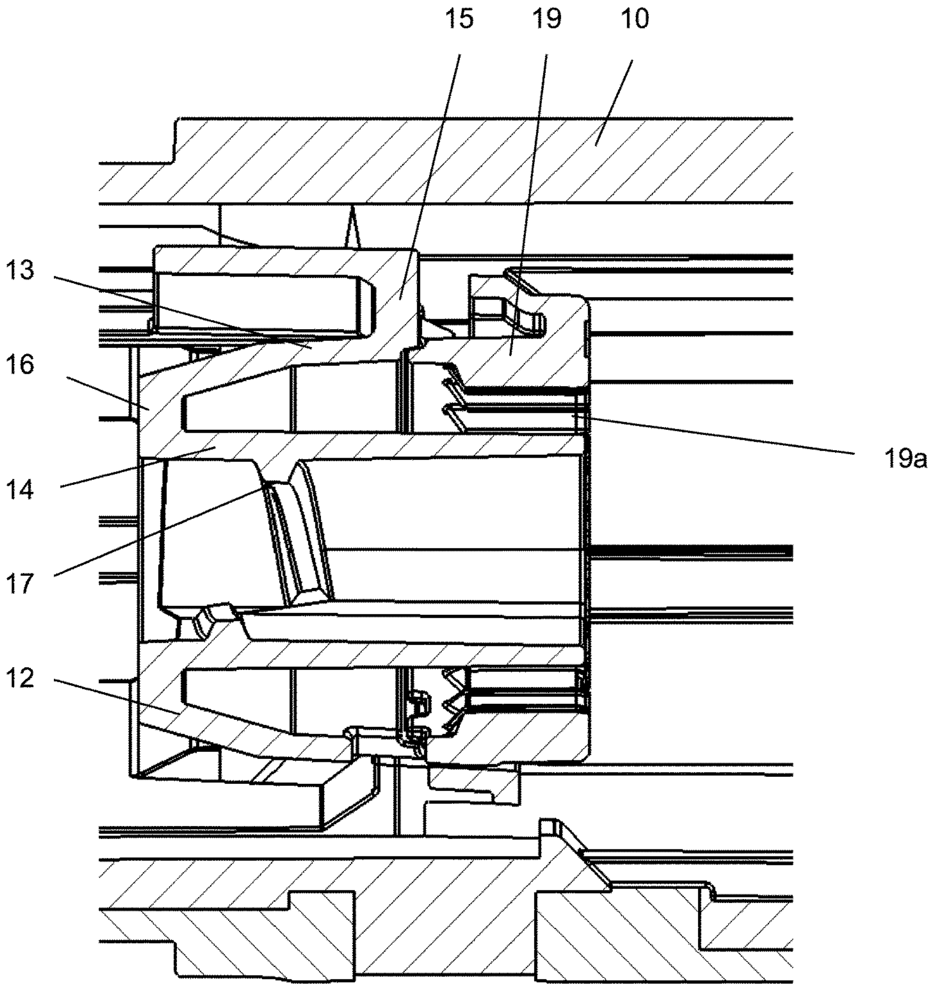
FIG. 5*a* shows in a sectional view a detail of a device according to a third embodiment of the present disclosure.
Figure 5B:
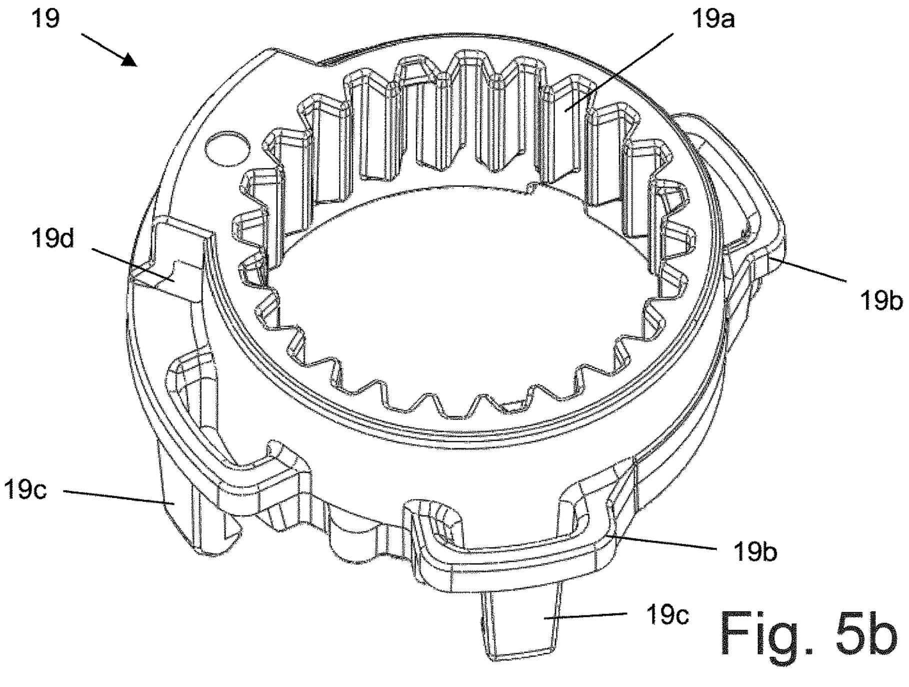
FIG. 5*b* shows a detail of the embodiment of FIG. 5*a*.

In the embodiment of FIGS. 5*a* and 5*b*, the insert 12 is partially formed as one single component part with the housing 10 and partially as a separate component part 19. The cup-shaped body 13 and the threaded tube 14 with the annular space for a compression spring are integrally formed with the housing 10 an connected thereto via arms 15, whereas the clutch feature 18 for rotationally constraining the drive member 40 is a separate ring-shaped component part 19 which is axially and rotationally constrained to the housing 10. Thus, according to the embodiment of FIGS. 5*a* and 5*b*, the ring-shaped insert part 19 does not have the thread 17 as an integral part. As shown in FIG. 5*b* in more detail, the ring-shaped insert part 19 comprises axially orientated splines 19*a* on an inner surface to rotationally restrain the drive member 40. The ring-shaped insert part 19 further comprises arms or splines 19*b* on its outer surface for rotational retention within the housing 10. Further, several hook-like arms 19*c* are provided to form a snap clip for axial retention of the ring-shaped insert part 19 within the housing 10. The ring-shaped insert part 19 comprises a hole or pocket 19*d* for receiving and fixing the hook end 91 of the drive spring 90. In addition, there are features on the ring-shaped insert part 19 that bias the insert parts 12, 19 axially and rotationally to remove free play.

The reservoir unit body 20 is located at the distal side of housing 10 and permanently attached thereto. The reservoir unit body may be a transparent or translucent component which is tubular to receive reservoir 100. The distal end of reservoir unit body 20 may be provided with means for attaching a needle arrangement. A removable cap (not shown) may be provided to fit over the reservoir unit body 20 and may be retained via clip features on the housing 10.

The piston rod 30 is rotationally constrained to the drive member 40 via a splined interface. When rotated, the piston rod 30 is forced to move axially relative to the drive member 40, through its threaded interface with the insert 12 of housing 10. The piston rod 30 is an elongate member with an outer thread engaging the corresponding thread of the insert 12 of housing 10. The interface comprises at least one longitudinal groove or track and a corresponding protrusion or spline of the drive member 40. At its distal end, the piston rod 30 is provided with an interface for clip attachment of the bearing 140.

The drive member 40 is a hollow member surrounding the piston rod 30 and arranged within dose setting member 60. It extends from an interface with the clutch plate 120 to the contact with the clutch spring 130. The drive member 40 is axially movable relative to the housing 10, the piston rod 30 and the dose setting member 60 in the distal direction against the bias of clutch spring 130 and in the opposite proximal direction under the bias of clutch spring 130.

Figure 3A:
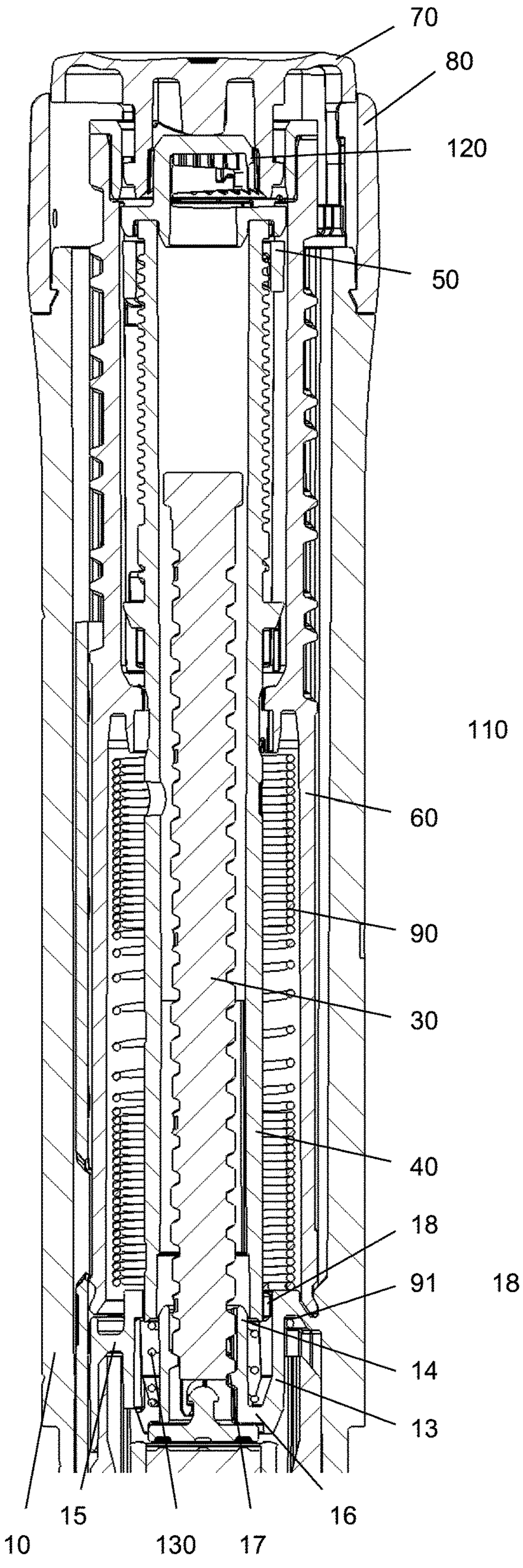
FIG. 3*a* shows a sectional view of the proximal end of the device of FIG. 1 in a setting state.

A splined tooth interface 18 with the insert 12 prevents rotation of the drive member 40 during dose setting. This interface comprises a ring of radially extending outer teeth 41 at the distal end of drive member 40 and corresponding radially extending inner teeth 18 of the housing component 10 (insert 12). When the button 70 is pressed (FIG. 3*b*), these drive member to housing insert spline teeth are disengaged allowing the drive member 40 to rotate relative to the insert and, thus, to housing 10. Clutch spring 130 biases the drive member 40 into a position engaging with its teeth 41 the teeth 18 of the insert (FIG. 3*a*). A further splined tooth interface with the dose setting member 60 is not engaged during dialling, but engages when the button 70 is pressed, preventing relative rotation between the drive member 40 and dose setting member 60 during dispense. In a preferred embodiment this interface comprises inwardly directed splines on a flange on the inner surface of the dose setting member 60 and a ring of radially extending outer splines of drive member 40. These corresponding splines are located on the dose setting member 60 and the drive member 40, respectively, such that axial movement of the drive member 40 relative to the (axially fixed) dose setting member 60 engages or disengages the splines to rotationally couple or decouple the drive member 40 and the dose setting member 60.

A further interface of the drive member 40 comprises a ring of ratchet teeth located at the proximal end face of drive member 40 and a ring of corresponding ratchet teeth on the clutch plate 120.

The drive member 40 has a threaded section providing a helical track for the nut 50. In addition, a last dose abutment or stop is provided which may be the end of the thread track or preferably a rotational hard stop for interaction with a corresponding last dose stop of nut 50, thus limiting movement of the nut 50 on the driver thread. At least one longitudinal spline of the drive member 40 engages a corresponding track of the piston rod 30.

The last dose nut 50 is located between the dose setting member 60 and the drive member 40. It is rotationally constrained to the dose setting member 60, via a splined interface. It moves along a helical path relative to the drive member 40, via a threaded interface, when relative rotation occurs between the dose setting member 60 and drive member 40 which is during dialling only. As an alternative, the nut 50 may be splined to the drive member 40 and threaded to the dose setting member 60. A last dose stop is provided on nut 50 engaging a stop of drive member 40 when a dose is set corresponding to the remaining dispensable amount of medicament in the reservoir 100.

The dose indicator or dose setting member 60 is a tubular element. The dose setting member 60 is rotated during dose setting (via dose selector 80) and dose correction and during dose dispensing by torsion spring 90. Together with gauge element 110 the dose setting member 60 defines a zero position ('at rest') and a maximum dose position. Thus, the dose setting member 60 may be seen as a dose setting member.

For manufacturing reasons the dose setting member 60 of the embodiment shown in the Figures comprises a dose setting member lower 60*a* which is rigidly fixed to a dose setting member upper 60*b* during assembly to form the dose setting member 60. Dose setting member lower 60*a* and dose setting member upper 60*b* are separate components only to simplify dose setting member 60 mould tooling and assembly. As an alternative, the dose setting member 60 may be a unitary component. The dose setting member 60 is constrained to the housing 10 by snap engagement to allow rotation but not translation. The dose setting member 60 comprises an annular recess or groove near its distal end which engages a corresponding bead on an inner surface of the housing 10. The dose setting member lower 60*a* is marked with a sequence of numbers, which are visible through the gauge element 110 and the openings 11*a*, 11*b* in the housing 10, to denote the dialed dose of medicament.

Further, the dose setting member lower 60*a* has a portion with an outer thread engaging the gauge element 110. End stops are provided at the opposite ends of thread to limit relative movement with respect to the gauge element 110.

Clutch features which have the form of a ring of splines are provided inwardly directed on dose setting member upper 60*b* for engagement with splines of the button 70 during dose setting and dose correction. A clicker arm is provided on the outer surface of dose setting member 60 which interacts with the drive member 40 and the gauge member 110 for generating a feedback signal. In addition, the dose setting member lower 60*a* is rotationally constrained to the nut 50 and to the clutch plate 120 via a splined interface comprising at least one longitudinal spline. Further, dose setting member lower 60*a* comprises an interface for attachment of the torsion spring 90.

The button 70 which forms the proximal end of the device is permanently splined to the dose selector 80. A central stem extends distally from the proximal actuation face of the button 70. The stem is provided with a flange carrying the splines for engagement with splines of the dose setting member upper 60*b*. Thus, it is also splined via splines to the dose setting member upper 60*b* when the button 70 is not pressed, but this spline interface is disconnected when the button 70 is pressed. The button 70 has a discontinuous annular skirt with splines. When the button 70 is pressed, splines on the button 70 engage with splines on the housing 10, preventing rotation of the button 70 (and hence the dose selector 80) during dispense. These splines disengage when the button 70 is released, allowing a dose to be dialed. Further, a ring of ratchet teeth is provided on the inner side of button flange for interaction with clutch plate 120.

The dose selector 80 is axially constrained to the housing 10. It is rotationally constrained, via the splined interface, to the button 70. This splined interface which includes grooves interacting with spline features formed by the annular skirt of button 70 remains engaged irrespective of the dose button 70 axial positions. The dose selector 80 or dose dial grip is a sleeve-like component with a serrated outer skirt.

The torsion spring 90 is attached at its distal end by a hook 91 to the insert 12 and, thus, to the housing 10 and at the other end to the dose setting member 60. The torsion spring 90 is located inside the dose setting member 60 and surrounds a distal portion of the drive member 40. The torsion spring 90 is pre-wound upon assembly, such that it applies a torque to the dose setting member 60 when the mechanism is at zero units dialed. The action of rotating the dose selector 80, to set a dose, rotates the dose setting member 60 relative to the housing 10, and charges the torsion spring 90 further.

The reservoir 100 is received in reservoir unit body 20. The reservoir 100 may be a glass ampoule having a moveable rubber bung at its proximal end. The distal end of reservoir 100 is provided with a pierceable rubber seal which is held in place by a crimped annular metal band. In the embodiment depicted in the Figures, the reservoir 100 is a standard 1.5 ml reservoir. The device is designed to be disposable in that the reservoir 100 cannot be replaced by the user or health care professional. However, a reusable variant of the device could be provided by making the reservoir unit body 20 removable and allowing backwinding of the piston rod 30 and the resetting of nut 50.

The gauge element 110 is constrained to prevent rotation but allow translation relative to the housing 10 via a splined interface. The gauge element 110 has a helical feature on its inner surface which engages with the helical thread cut in the dose setting member 60 such that rotation of the dose setting member 60 causes axial translation of the gauge element 110. This helical feature on the gauge element 110 also creates stop abutments against the end of the helical cut in the dose setting member 60 to limit the minimum and maximum dose that can be set.

The gauge element 110 has a generally plate or band like component having a central aperture or window and two flanges extending on either side of the aperture. The flanges are preferably not transparent and thus shield or cover the dose setting member 60, whereas the aperture or window allows viewing a portion of the dose setting member lower 60*a*. Further, gauge element 110 has a cam and a recess interacting with the clicker arm of the dose setting member 60 at the end of dose dispensing.

The clutch plate 120 is a ring-like component. The clutch plate 120 is splined to the dose setting member 60 via splines. It is also coupled to the drive member 40 via a ratchet interface. The ratchet provides a detented position between the dose setting member 60 and drive member 40 corresponding to each dose unit, and engages different ramped tooth angles during clockwise and anti-clockwise relative rotation. A clicker arm is provided on the clutch plate 120 for interaction with ratchet features of the button 70.

The clutch spring 130 is a compression spring. The axial position of the drive member 40, clutch plate 120 and button 70 is defined by the action of the clutch spring 130, which applies a force on the drive member 40 in the proximal direction. This spring force is reacted via the drive member 40, clutch plate 120, and button 70, and when 'at rest' it is further reacted through the dose selector 80 to the housing 10. The spring force ensures that the ratchet interface between drive member 40 and clutch plate 120 is always engaged. In the 'at rest' position, it also ensures that the button splines are engaged with the dose setting member splines, and the drive member teeth are engaged with teeth of the housing 10.

The bearing 140 is axially constrained to the piston rod 30 and acts on the bung within the liquid medicament reservoir. It is axially clipped to the piston rod 30, but free to rotate.

With the device in the 'at rest' condition as shown in FIGS. 1 and 3*a*, the dose setting member 60 is positioned against its zero dose abutment with the gauge element 110 and the button 70 is not depressed. Dose marking '0' on the dose setting member 60 is visible through the window 11*b* of the housing 10 and gauge element 110, respectively.

The torsion spring 90, which has a number of pre-wound turns applied to it during assembly of the device, applies a torque to the dose setting member 60 and is prevented from rotating by the zero dose abutment.

The user selects a variable dose of liquid medicament by rotating the dose selector 80 clockwise, which generates an identical rotation in the dose setting member 60. Rotation of the dose setting member 60 causes charging of the torsion spring 90, increasing the energy stored within it. As the dose setting member 60 rotates, the gauge element 110 translates axially due to its threaded engagement thereby showing the value of the dialed dose. The gauge element 110 has flanges either side of the window area which cover the numbers printed on the dose setting member 60 adjacent to the dialed dose to ensure only the set dose number is made visible to the user.

A specific feature of this disclosure is the inclusion of a visual feedback feature in addition to the discrete dose number display typical on devices of this type. The distal end of the gauge element 110 creates a sliding scale through the small window 11*a* in the housing 10. As an alternative, the sliding scale could be formed using a separate component engaged with the dose setting member 60 on a different helical track.

As a dose is set by the user, the gauge element 110 translates axially, the distance moved proportional to the magnitude of the dose set. This feature gives clear feedback to the user regarding the approximate size of the dose set. The dispense speed of an auto-injector mechanism may be higher than for a manual injector device, so it may not be possible to read the numerical dose display during dispense. The gauge feature provides feedback to the user during dispense regarding dispense progress without the need to read the dose number itself. For example, the gauge display may be formed by an opaque element on the gauge element 110 revealing a contrasting coloured component underneath. Alternatively, the revealable element may be printed with coarse dose numbers or other indices to provide more precise resolution. In addition, the gauge display simulates a syringe action during dose set and dispense.

The drive member 40 is prevented from rotating as the dose is set and the dose setting member 60 rotated, due to the engagement of its splined teeth with teeth of the housing 10. Relative rotation must therefore occur between the clutch plate 120 and drive member 40 via the ratchet interface.

The user torque required to rotate the dose selector 80 is a sum of the torque required to wind up the torsion spring 90, and the torque required to overhaul the ratchet interface. The clutch spring 130 is designed to provide an axial force to the ratchet interface and to bias the clutch plate 120 onto the drive member 40. This axial load acts to maintain the ratchet teeth engagement of the clutch plate 120 and drive member 40. The torque required to overhaul the ratchet in the dose set direction is a function of the axial load applied by the clutch spring 130, the clockwise ramp angle of the ratchet teeth, the friction coefficient between the mating surfaces and the mean radius of the ratchet interface.

As the user rotates the dose selector 80 sufficiently to increment the mechanism by one increment, the dose setting member 60 rotates relative to the drive member 40 by one ratchet tooth. At this point the ratchet teeth re-engage into the next detented position. An audible click is generated by the ratchet re-engagement, and tactile feedback is given by the change in torque input required.

Relative rotation of the dose setting member 60 and the drive member 40 is allowed. This relative rotation also causes the last dose nut 50 to travel along its threaded path, towards its last dose abutment on the drive member 40.

With no user torque applied to the dose selector 80, the dose setting member 60 is now prevented from rotating back under the torque applied by the torsion spring 90, solely by the ratchet interface between the clutch plate 120 and the drive member 40. The torque necessary to overhaul the ratchet in the anti-clockwise direction is a function of the axial load applied by the clutch spring 130, the anti-clockwise ramp angle of the ratchet, the friction coefficient between the mating surfaces and the mean radius of the ratchet features. The torque necessary to overhaul the ratchet must be greater than the torque applied to the dose setting member 60 (and hence clutch plate 120) by the torsion spring 90. The ratchet ramp angle is therefore increased in the anti-clockwise direction to ensure this is the case whilst ensuring the dial-up torque is as low as possible.

The user may now choose to increase the selected dose by continuing to rotate the dose selector 80 in the clockwise direction. The process of overhauling the ratchet interface between the dose setting member 60 and drive member 40 is repeated for each dose increment. Additional energy is stored within the torsion spring 90 for each dose increment and audible and tactile feedback is provided for each increment dialed by the re-engagement of the ratchet teeth. The torque required to rotate the dose selector 80 increases as the torque required to wind up the torsion spring 90 increases. The torque required to overhaul the ratchet in the anti-clockwise direction must therefore be greater than the torque applied to the dose setting member 60 by the torsion spring 90 when the maximum dose has been reached.

If the user continues to increase the selected dose until the maximum dose limit is reached, the dose setting member 60 engages with its maximum dose abutment on the maximum dose abutment of gauge element 110. This prevents further rotation of the dose setting member 60, clutch plate 120 and dose selector 80.

Depending on how many unit increments of drug have already been delivered by the mechanism, during selection of a dose, the last dose nut 50 may contact its last dose abutment with a stop face of the drive member 40. The abutment prevents further relative rotation between the dose setting member 60 and the drive member 40, and therefore limits the dose that can be selected. The position of the last dose nut 50 is determined by the total number of relative rotations between the dose setting member 60 and drive member 40, which have occurred each time the user sets a dose.

With the mechanism in a state in which a dose has been selected, the user is able to deselect any number of increments from this dose. Deselecting a dose is achieved by the user rotating the dose selector 80 anti-clockwise. The torque applied to the dose selector 80 by the user is sufficient, when combined with the torque applied by the torsion spring 90, to overhaul the ratchet interface between the clutch plate 120 and drive member 40 in the anti-clockwise direction. When the ratchet is overhauled, anti-clockwise rotation occurs in the dose setting member 60 (via the clutch plate 120), which returns the dose setting member 60 towards the zero dose position, and unwinds the torsion spring 90. The relative rotation between the dose setting member 60 and drive member 40 causes the last dose nut 50 to return along its helical path, away from the last dose abutment.

Figure 3B:
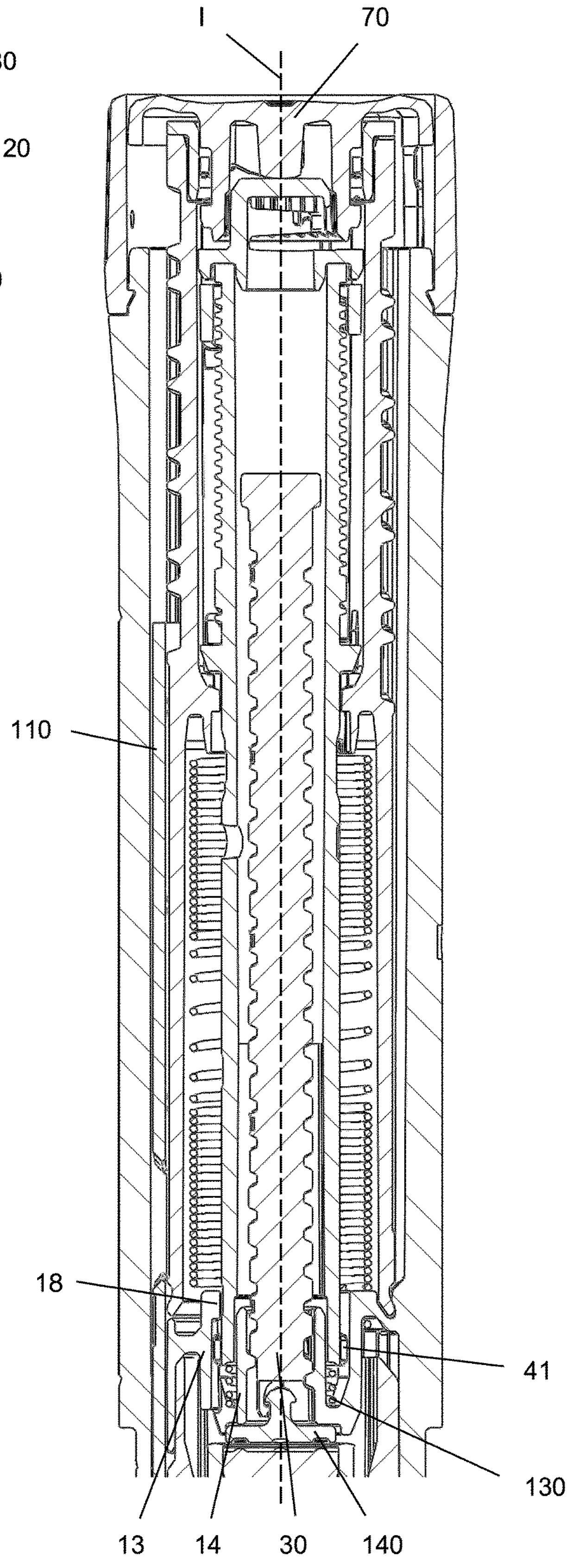
FIG. 3*b* shows a sectional view of the proximal end of the device of FIG. 1 in a dose delivery state.

With the mechanism in a state in which a dose has been selected, the user is able to activate the mechanism to commence delivery of a dose. Delivery of a dose is initiated by the user depressing the button 70 axially in the distal direction (FIG. 3*b*).

When the button 70 is depressed, splines between the button 70 and dose setting member 60 are disengaged, rotationally disconnecting the button 70 and dose selector 80 from the delivery mechanism, i.e. from dose setting member 60, gauge element 110 and torsion spring 90. Splines on the button 70 engage with splines on the housing 10, preventing rotation of the button 70 (and hence the dose selector 80) during dispense. As the button 70 is stationary during dispense, it can be used in the dispense clicker mechanism. A stop feature in the housing 10 limits axial travel of the button 70 and reacts any axial abuse loads applied by the user, reducing the risk of damaging internal components.

The clutch plate 120 and drive member 40 travel axially with the button 70. This engages the splined tooth interface between the drive member 40 and dose setting member 60, preventing relative rotation between the drive member 40 and dose setting member 60 during dispense. The splined tooth interface 18, 41 between the drive member 40 and the housing insert 12 disengages, so the drive member 40 can now rotate and is driven by the torsion spring 90 via the dose setting member 60, and clutch plate 120.

Rotation of the drive member 40 causes the piston rod 30 to rotate due to their splined engagement, and the piston rod 30 then advances due to its threaded engagement to the housing 10. The dose setting member 60 rotation also causes the gauge element 110 to traverse axially back to its zero position whereby the zero dose abutment stops the mechanism.

Tactile feedback during dose dispense is provided via the compliant cantilever clicker arm integrated into the clutch plate 120. This arm interfaces radially with ratchet features on the inner surface of the button 70, whereby the ratchet tooth spacing corresponds to the dose setting member 60 rotation required for a single increment dispense. During dispense, as the dose setting member 60 rotates and the button 70 is rotationally coupled to the housing 10, the ratchet features engage with the clicker arm to produce an audible click with each dose increment delivered.

Delivery of a dose continues via the mechanical interactions described above while the user continues to depress the button 70. If the user releases the button 70, the clutch spring 130 returns the drive member 40 to its 'at rest' position (together with the clutch plate 120 and button 70), engaging the splines between the drive member 40 and housing 10, preventing further rotation and stopping dose delivery.

During delivery of a dose, the drive member 40 and dose setting member 60 rotate together, so that no relative motion in the last dose nut 50 occurs. The last dose nut 50 therefore travels axially relative to the drive member 40 during dialling only.

Once the delivery of a dose is stopped, by the dose setting member 60 returning to the zero dose abutment, the user may release the button 70, which will re-engage the spline teeth between the drive member 40 and housing 10. The mechanism is now returned to the 'at rest' condition.

At the end of dose dispensing, additional audible feedback is provided in the form of a 'click', distinct from the 'clicks' provided during dispense, to inform the user that the device has returned to its zero position via the interaction of the clicker arm on the dose setting member 60 with the ramp on the drive member 40 and the cam and the recess on the gauge element 110. This embodiment allows feedback to only be created at the end of dose delivery and not created if the device is dialed back to, or away from, the zero position.

FIGS. 6*a*, 6*b*, 7*a*, and 7*b* show schematic sectional views of a region of a mechanism unit for the drug delivery device of various alternative embodiments of the drive member 40 in conjunction with the piston rod 30 and the clutch spring 130. These embodiments allow for the exact adjustment of the position of the piston rod 30 relative to the housing 10 prior to the final assembly of the drug delivery device. The device may be the one described further above. Accordingly, the features described in FIGS. 1-5 may be used for the embodiments described below. The drug delivery device may be disposable or it may be reusable. In the embodiments of the FIGS. 6*a*, 6*b*, 7*a*, 7*b*, 9*a*, 9*b*, 9*c*, 9*d*, 10*a*, 10*b*, 10*c*, and 10*d* the mechanism unit comprises the housing 10, the piston rod 30, wherein the piston rod 30 is movably retained in the housing 10, and a dose setting and drive mechanism which is configured to perform a dose setting operation for setting a dose to be delivered and a dose delivery operation for delivering the set dose by transferring a delivery force to the piston rod 30 in order to drive the piston rod 30 in the distal direction relative to the housing 10 in the dose delivery operation.

The terms "distal" and "proximal" as used herein may refer to opposite axial directions or ends. "Distal" may refer to a direction towards a dispensing end or an end of a component of the drug delivery device which is or is to be arranged closest to the dispensing end of the reservoir 100, the reservoir unit body 20 or the drug delivery device. "Proximal" may refer to a direction away from the dispensing end or an end which is or is to be arranged further away from the dispensing end of the reservoir 100, the reservoir unit body 20 or the drug delivery device. Moreover, the distal direction may be away from the proximal end. The proximal direction may be away from the distal end.

The dose setting and drive mechanism comprises the drive member 40 and a clutch mechanism. In contrast to the previously described configuration where the drive member was unitary, the drive member 40 in the embodiments of the FIGS. 6*a*, 6*b*, 7*a*, 7*b*, 9*a*, 9*b*, 9*c*, 9*d*, 10*a*, 10*b*, 10*c*, and 10*d* is a two-part component comprising a first drive member 40*a* and a second drive member 40*b*. The piston rod 30 is movable relative to the housing 10, e.g. movably retained in the housing 10 (not shown in FIGS. 6*a*, 6*b*, 7*a*, 7*b*, 9*a*, 9*b*, 9*c*, 9*d*, 10*a*, 10*b*, 10*c*, and 10*d*). The first drive member 40*a* is in direct mechanical cooperation with the piston rod 30 due to a lock 44 (as shown in FIGS. 6*a*, 6*b*, 7*a*, 7*b*, 10*a*, and 10*b*) or a thread guide 45 (as shown in FIGS. 9*a*, 9*b*, 9*c*, and 9*d*) to transfer a force to the piston rod 30, wherein the lock 44 and the thread guide 45 may be integral components of the first drive member 40*a*. The first drive member 40*a* is axially secured and rotatable relative to the housing 10, wherein rotation of the first drive member 40*a* in a delivery direction relative to the housing 10 results in movement of the piston rod 30 in the distal direction and rotation in the direction opposite to the delivery direction results in proximal movement of the piston rod 30. The second drive member 40*b* is arranged to be mechanically, preferably directly, coupled to the first drive member 40*a* to transfer the delivery force to the first drive member 40*a*. As shown in the embodiments of FIGS. 6*a*, 6*b*, 7*a*, 7*b*, 10*a*, and 10*b*, the first drive member 40*a* may be splined to the piston rod and the piston rod may be threadedly coupled to the housing. Alternatively, as shown in FIGS. 9*a*, 9*b*, 9*c*, and 9*d*, the first drive member 40*a* may be threadedly coupled to the piston rod and the piston rod may be splined to the housing.

The clutch mechanism comprises the clutch spring 130. The distal end of the clutch spring 130 rests on the first driver member 40*a* and the proximal end of the clutch spring 130 rests on the second driver member 40*b*, so that axial movement in distal direction of the second driver member 40*b* relative to the first driver member 40*a* can only occur against the resistance of the spring force of the clutch spring 130. The clutch mechanism has at least two different states, a delivery state where the clutch spring 130 is compressed (see FIGS. 6*b*, 7*b*, 9*a*, and 10*b*) and a setting state where the clutch spring 130 is less compressed than in the delivery state (see FIGS. 6*a*, 7*a*, 9*b*, and 10*a*).

In the setting state, the second drive member 40*b* is rotationally secured with respect to the housing 10 at least against rotation in the delivery direction. The second drive member 40*b* may be rotationally secured with respect to the housing 10 in the same manner as the one-piece drive member 40 described in FIGS. 1-5. However, in the setting state, it is also conceivable that the second drive member 40*b* is rotationally secured with respect to the housing 10 against rotation in the delivery direction and in the direction opposite to the delivery direction. In the delivery state, the second drive member 40*b* is rotatable relative to the housing 10 in the delivery direction, wherein, in the setting state, the first drive member 40*a* is rotatable relative to the second drive member 40*b* and the housing 10 at least in the delivery direction, and wherein, in the delivery state, the second drive member 40*b* is rotationally locked to the first drive member 40*a* at least against rotation of the second drive member 40*b* relative to the first drive member 40*a* in the delivery direction. However, in the delivery state, it is also conceivable that the second drive member 40*b* is rotationally locked to the first drive member 40*a* against rotation of the second drive member 40*b* relative to the first drive member 40*a* in the delivery direction and in the direction opposite to the delivery direction.

The mechanism unit is configured to be connected to the reservoir unit comprising the reservoir 100 and the reservoir unit body 20 for assembling the two units. The first drive member 40*a* is accessible from the exterior of the housing 10 for manipulations such that, in the setting state, the position of the piston rod 30 relative to the housing 10 can be adjusted by rotation of the first drive member 40*a* before the mechanism unit and the reservoir unit are connected. This accessibility can be through any one of or both the distal end and the proximal end of the housing 10. However, it is also conceivable that the first drive member 40*a* can be accessed from the outside of the housing 10 before the drug delivery device is fully assembled and after the mechanism unit and the reservoir unit are connected. In this case, the first drive member 40*a* is accessible from the proximal end of the housing 10 via an opening which is closed by the button 70 during final assembly of the drug delivery device. It goes without saying that this opening can also be used to manipulate the first drive member 40*a* before the mechanism unit is connected to the reservoir unit.

In the embodiments of the FIGS. 6*a*, 6*b*, 7*a*, 7*b*, 9*a*, 9*b*, 9*c*, 9*d*, 10*a*, 10*b*, 10*c*, and 10*d* the second drive member 40*b* is axially movable relative to the first drive member 40*a* and the housing 10, e.g. in the distal direction, for switching between the setting state, as shown in FIGS. 6*a*, 7*a*, 9*b*, and 10*a*, and the delivery state, as shown in FIGS. 6*b*, 7*b*, 9*a*, and 10*b*. Furthermore, the first drive member 40*a* is secured against proximal and distal movement relative to the housing 10 in the setting and delivery state.

The first drive member 40*a* is engaged to the piston rod 30 and the piston rod 30 is engaged to the housing 10. In the embodiments of the FIGS. 6*a*, 6*b*, 7*a*, 7*b*, 10*a*, and 10*b* the first drive member 40*a* is directly splined to the piston rod 30 due to the lock 44 and the piston rod 30 is threadedly engaged to the housing 10. In this case, no rotational movement of the first drive member 40*a* relative to the piston rod 30 in the setting and delivery state is possible.

As shown in the FIGS. 6*a*, 6*b*, 7*a*, and 7*b* the first drive member 40*a* comprises a first locking feature 42 and the second drive member 40*b* comprises a second locking feature 43. The first locking feature 42 is rotationally and axially immovably relative to the first drive member 40*a* and the second locking feature 43 is rotationally and axially immovably relative to the second drive member 40*b*. The first locking feature 42 may be an integral part of the first drive member 40*a* and the second locking feature 43 may be an integral part of the second drive member 40*b*.

Figure 6A:
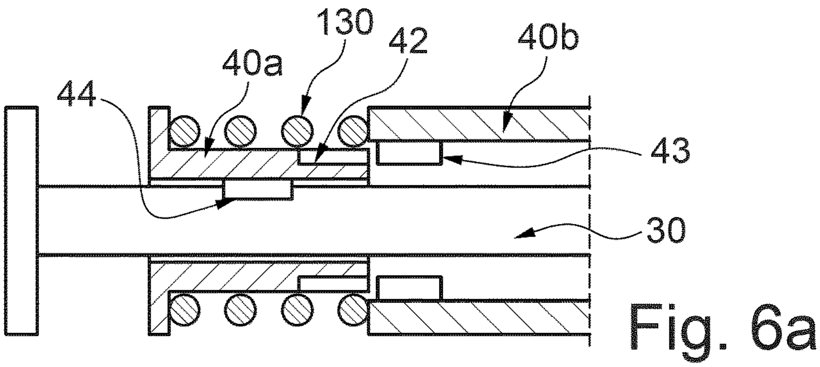
FIG. 6*a* shows a sectional view of an embodiment of a drive member in a setting state.
Figure 6B:
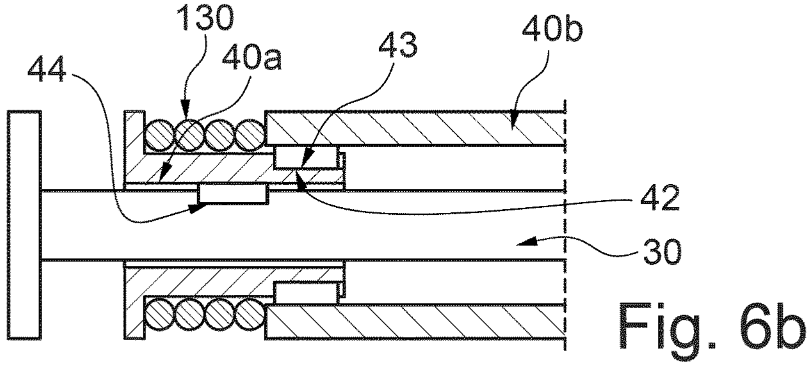
FIG. 6*b* shows a sectional view of the drive member of FIG. 6*a* in a delivery state.
Figure 7A:
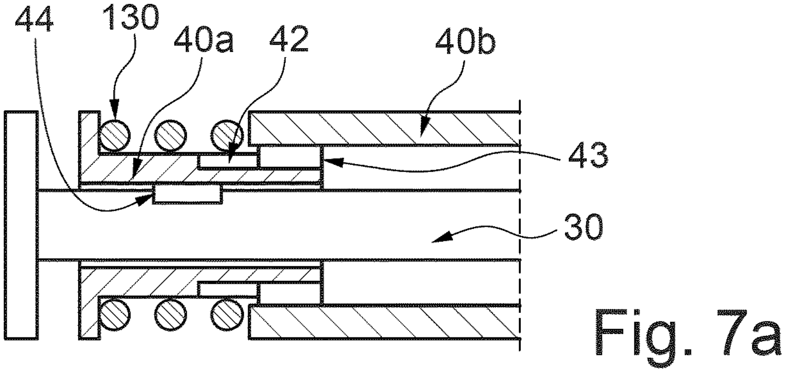
FIG. 7*a* shows a sectional view of another embodiment of a drive member in a setting state.
Figure 7B:
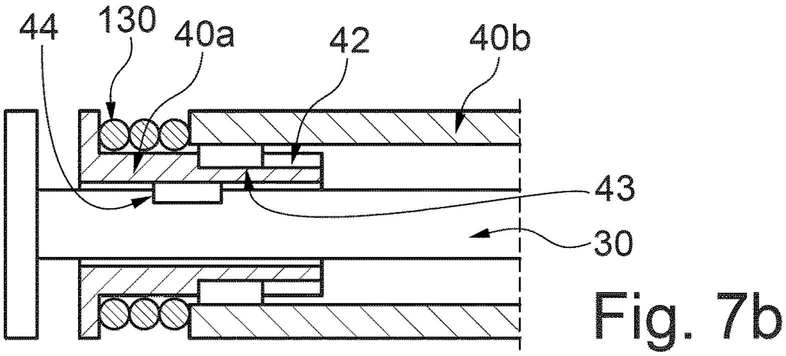
FIG. 7*b* shows a sectional view of the drive member of FIG. 7*a* in a delivery state.

As shown in the FIGS. 6*b* and 7*b* the first locking feature 42 is engaged with the second locking feature 43 in the delivery state.

FIGS. 6*a* and 6*b* show an embodiment of a mechanism unit, wherein, in the setting state, the first locking feature 42 and the second locking feature 43 are disengaged.

FIG. 6*a* shows the mechanism unit in the setting state. In this state the clutch spring 130 is relaxed and the first drive member 40*a* is not engaged with the second drive member 40*b*. Due to the detached connection of the first locking feature 42 and second locking feature 43, the first drive member 40*a* and the piston rod 30 can be rotated relative to the second drive member 40*b* in the delivery direction and in the direction opposite to the delivery direction. This makes it possible to move the piston rod 30 axially in both the proximal and distal directions with the help of the first drive member 40*a*, allowing the distance between proximal end of the bung and the distal end of the piston rod 30 to be individually adjusted. In this state, the second drive member 40*b* is not rotatory movable in relation to the housing 10.

FIG. 6*b* shows the mechanism unit according to the same embodiment as shown in FIG. 6*a* in the delivery state. In this state, the second drive member 40*b* is axially displaced in the distal direction due to the button 70 being pressed. This causes the clutch spring 130 to be compressed and the first locking feature 42 to engage with the second locking feature 43. Due to the resulting connection between the first locking feature 42 and second locking feature 43, the first drive member 40*a* is immovable relative to the second drive member 40*b* in the delivery direction and in the direction opposite to the delivery direction. Therefore a rotation of the second drive member 40*b* leads to a rotation of the first drive member 40*a*, whereby the piston rod 30 is axially displaced in the distal direction in order to be able to dispense the drug from the reservoir 100. After the button 70 is pressed, the spring force of the clutch spring 130 causes the second drive member 40*b* to move back to its original position in the setting mode.

In the embodiment shown in FIGS. 6*a* and 6*b*, the first locking feature 42 is designed as a circumferential outer ring on the outer circumferential surface at the proximal end of the first drive member 40*a*, the second locking feature 43 being arranged as a circumferential inner ring on the inner circumferential surface at the distal end of the second drive member 40*b*. The two rings have complementary locking wedges to each other. In setting mode, these locking wedges are pushed into each other in the axial direction so that no relative rotational movement is possible between the first locking feature 42 and the second locking feature 43.

The locking wedges of the second locking feature 43 may be tapered at their distal ends. Additionally or alternatively, the locking wedges of the first locking feature 42 may be tapered at their proximal ends. The tapers are designed to facilitate the insertion of the second locking feature 43 into the first locking feature 42 during the transition from the setting state to the delivery state.

The embodiment shown in the FIGS. 6*a* and 6*b* is particularly advantageous as it allows the position of the piston rod 30 to be changed axially in the distal and proximal directions in the setting state.

FIGS. 7*a* and 7*b* show an alternative embodiment of a mechanism unit, wherein the first locking feature 42 is engaged with the second locking feature 43 in the setting state (see FIG. 7*a*) and in the delivery state (see FIG. 7*b*).

In this case the first locking feature 42 and the second locking feature 43 are configured, such that the first locking feature 42 is rotatable relative to the second locking feature 43 in the delivery direction and rotationally secured with respect to the second locking feature 43 in the direction opposite to the delivery direction, if the first locking feature 42 is engaged with the second locking feature 43. The first locking feature 42 is designed as a circumferential outer ring on the outer circumferential surface at the proximal end of the first drive member 40*a*, the second locking feature 43 being arranged as a circumferential inner ring on the inner circumferential surface at the distal end of the second drive member 40*b*. The two rings have complementary saw-toothed wedges (see FIG. 8) which in both, the setting mode and the delivery mode, permit rotation of the first drive member 40*a* relative to the second drive member 40*b* in the delivery direction and prevent rotation of the first drive member 40*a* relative to the second drive member 40*b* in the direction opposite to the delivery direction.

Figure 8:
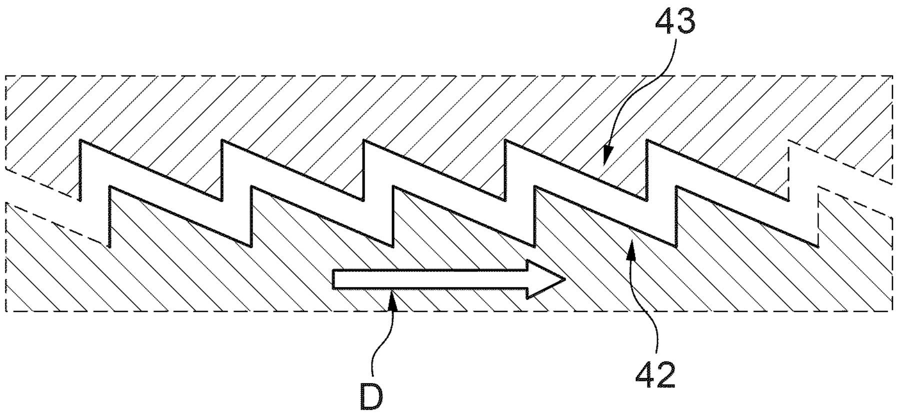
FIG. 8 shows a schematic view of an interface in a drive member.

As shown in FIG. 8, the first locking feature 42 or/and the second locking feature 43 is made elastic so that the saw-toothed wedges of the first locking feature 42 can slide over the saw-toothed wedges of the second locking feature 43 when the first locking feature 42 is moved in the delivery direction D. However, in this case it is not possible to slide the saw-toothed wedges of the first locking feature 42 over the saw-toothed wedges of the second locking feature 43 in the direction opposite to the delivery direction D. Consequently, in this case a movement of the saw-toothed wedges of the second locking feature 43 of the second driver member 40*b* in the delivery direction D inevitably leads to a movement of the saw-toothed wedges of the first locking feature 42 of the first drive member 40*a* in the delivery direction D. It should be noted that other interlocking mechanisms are also possible between the first locking feature 42 and the second locking feature 43 to achieve the above mentioned effect. For example, the use of other ratchet connections or the use of pawls could be conceivable.

Due to the saw-tooth connection, as shown in FIGS. 7*a*, 7*b*, and 8, it is not necessary to release the first drive member 40*a* of the second drive member 40*b* in the setting mode in order to axially displace the piston rod 30 in the distal direction by means of a rotary movement of the first drive member 40*a*. Thus, in contrast to the embodiment of FIGS. 6*a* and 6*b*, an insertion step of the first locking feature 42 with respect to the second locking feature 43 during the transition from the setting mode to the delivery mode can be avoided. Furthermore, after setting the desired distance between the proximal end of the bung and the distal end of the piston rod 30, the saw-tooth connection prevents axial displacement of the piston rod 30 in the proximal direction, since rotational movement of the first drive member 40*a* in the direction opposite to the delivery direction is not possible.

It should be noted however, that it is also conceivable that the first locking feature 40*a* and second locking feature 40*b* of the embodiment of FIGS. 6*a* and 6*b*, can be made as a saw-tooth connection.

As in the embodiment of FIGS. 6*a* and 6*b*, in the embodiment of FIGS. 7*a* and 7*b*, the second drive member 40*b* is rotationally locked relative to the housing 10 in the setting state and rotationally movable in delivery state.

FIGS. 9*a*, 9*b*, 9*c*, 9*d* and 10*a*, 10*b*, 10*c*, 10*d* each show a further embodiment of the two-part drive member 40 of a mechanism unit for a drug delivery device according to the disclosure, wherein FIGS. 9*a*, 9*b*, 10*a*, and 10*b* show longitudinal-section views and FIGS. 9*c*, 9*d*, 10*c*, and 10*d* show cross-sectional views of the drive member 40. The drug delivery device may be the one described further above. Accordingly, the features described in FIGS. 1-5 may be used for the embodiments described below. The drive member 40 comprises the first drive member 40*a* and the second drive member 40*b*, wherein the first drive member 40*a* comprises the first locking feature 42 and the second drive member 40*b* comprises the second locking feature 43. The first locking feature 42 is rotationally and axially immovably relative to the first drive member 40*a* and the second locking feature 43 is rotationally and axially immovably relative to the second drive member 40*b*. The first locking feature 42 may be an integral part of the first drive member 40*a* and the second locking feature 43 may be an integral part of the second drive member 40*b*. The first locking feature 42 is engaged with the second locking feature 43 in the delivery state (see FIGS. 9*a* and 10*b*) and in the setting state (see FIGS. 9*b* and 10*a*). The embodiments of FIGS. 9*a*, 9*b*, 9*c*, 9*d* and 10*a*, 10*b*, 10*c*, 10*d* differ only in that the first drive member 40*a* of FIGS. 9*a*, 9*b*, 9*c*, and 9*d* is splined to the piston rod 30 and the piston rod 30 is threadedly coupled to the housing 10 and the first drive member 40*a* of FIGS. 10*a*, 10*b*, 10*c*, and 10*d* is threadedly coupled to the piston rod 30 and the piston rod 30 is splined to the housing 10.

Figure 9A:
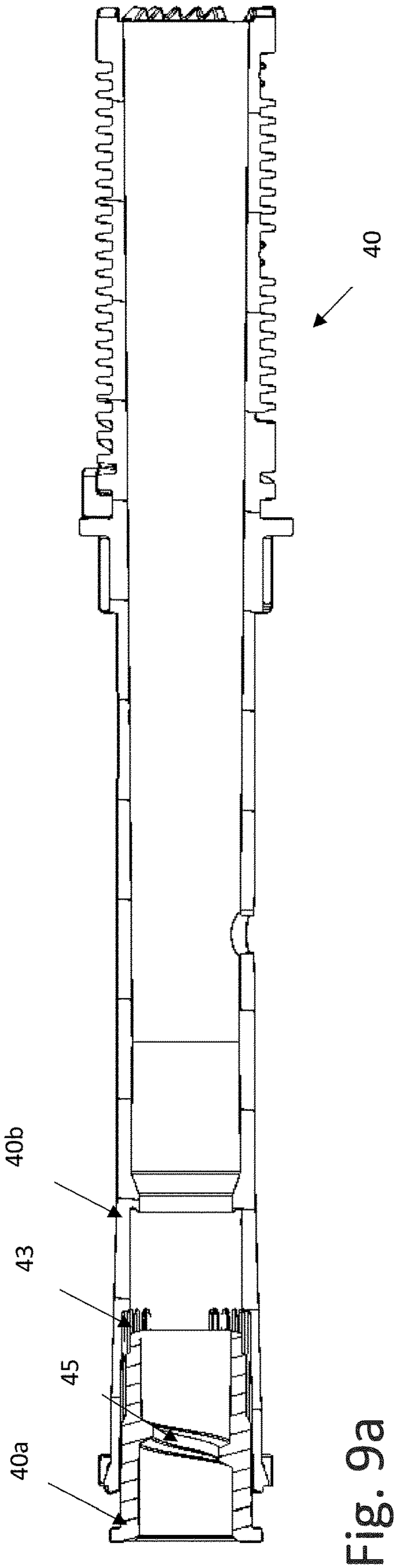
FIG. 9*a* shows a sectional view of yet another embodiment of a drive member in a delivery state.
Figure 9B:
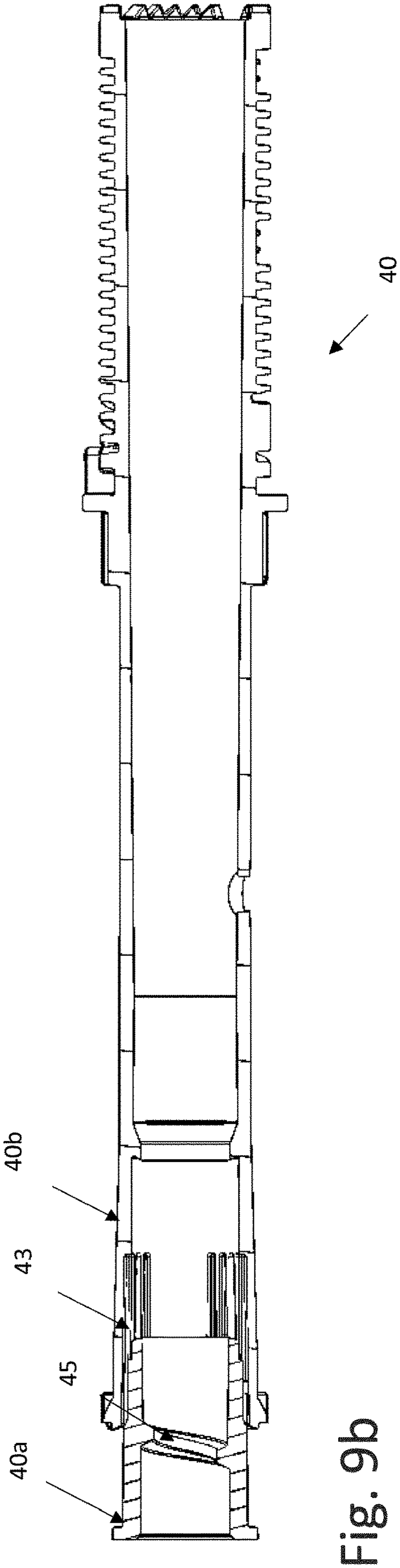
FIG. 9*b* shows a sectional view of the embodiment of FIG. 9*a* in a setting state.
Figure 9D:
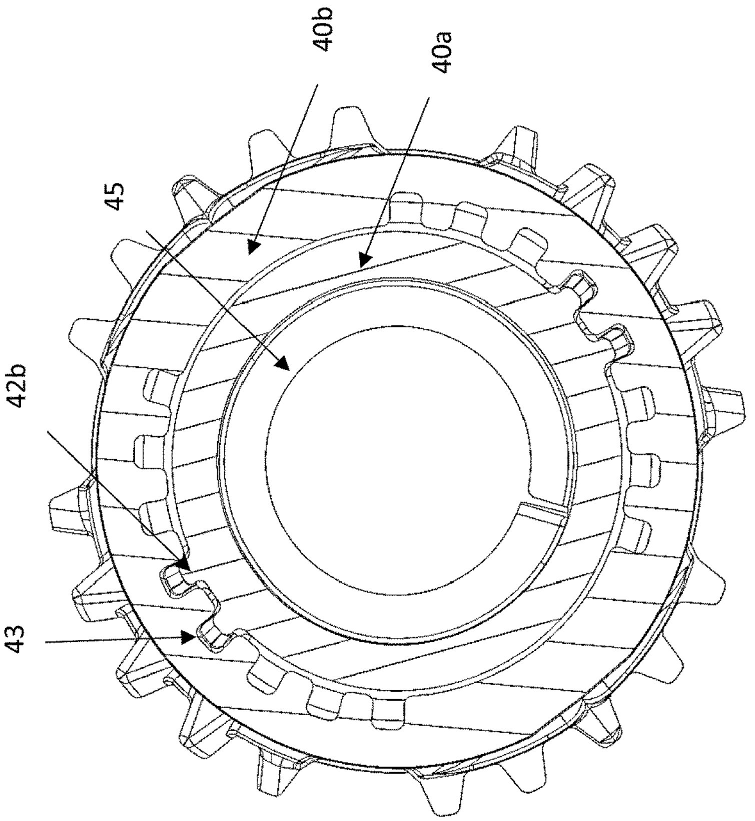
FIG. 9*d* shows yet another sectional view of the embodiment of FIGS. 9*a* and 9*b;*
Figure 9C:
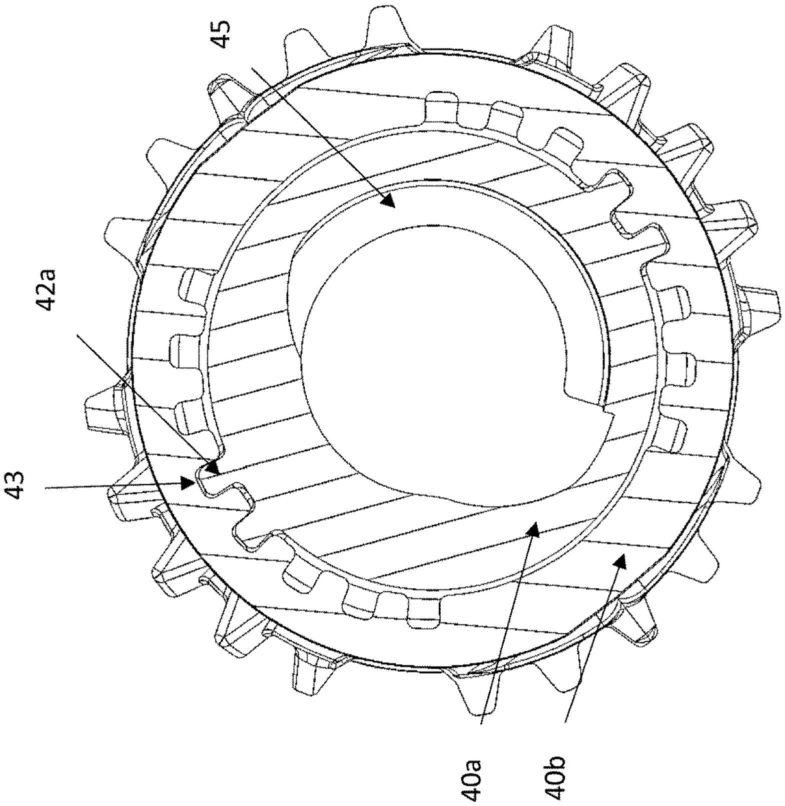
FIG. 9*c* shows a further sectional view of the embodiment of FIGS. 9*a* and 9*b;*
Figure 10A:
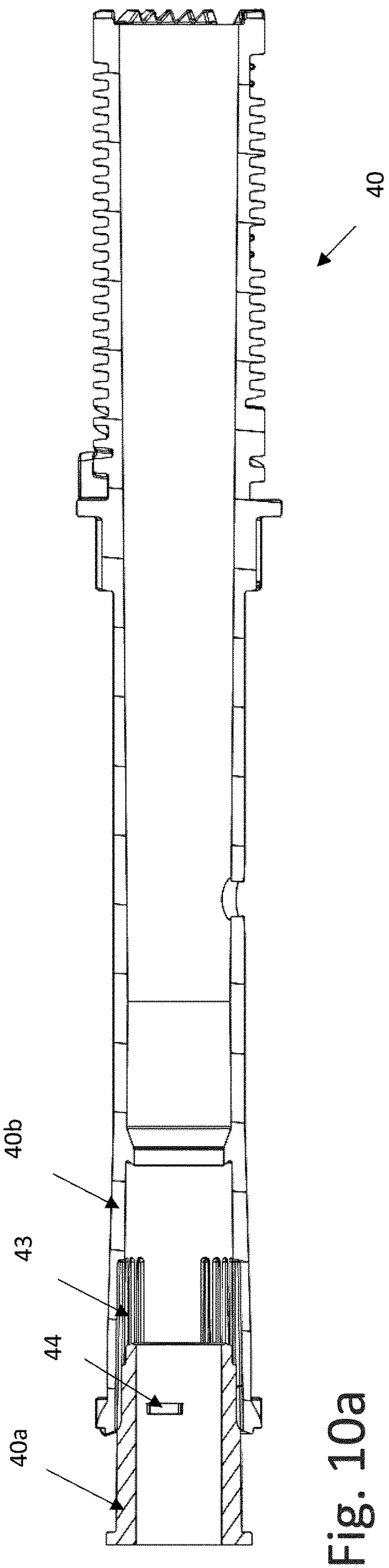
FIG. 10*a* shows a sectional view of yet another embodiment of a drive member in a setting state.
Figure 10B:
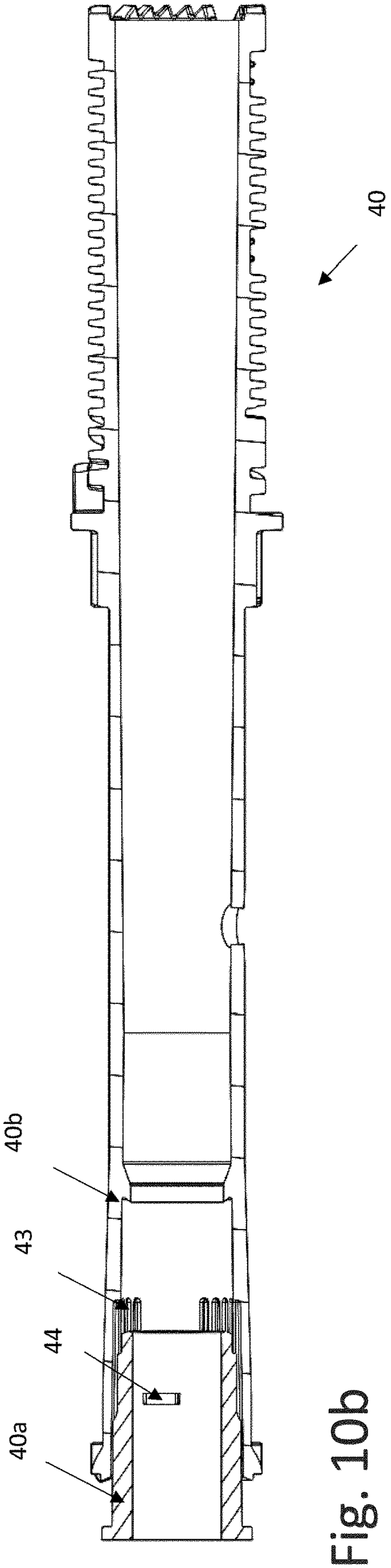
FIG. 10*b* shows a sectional view of the embodiment of FIG. 10*a* in a delivery state.
Figure 10D:
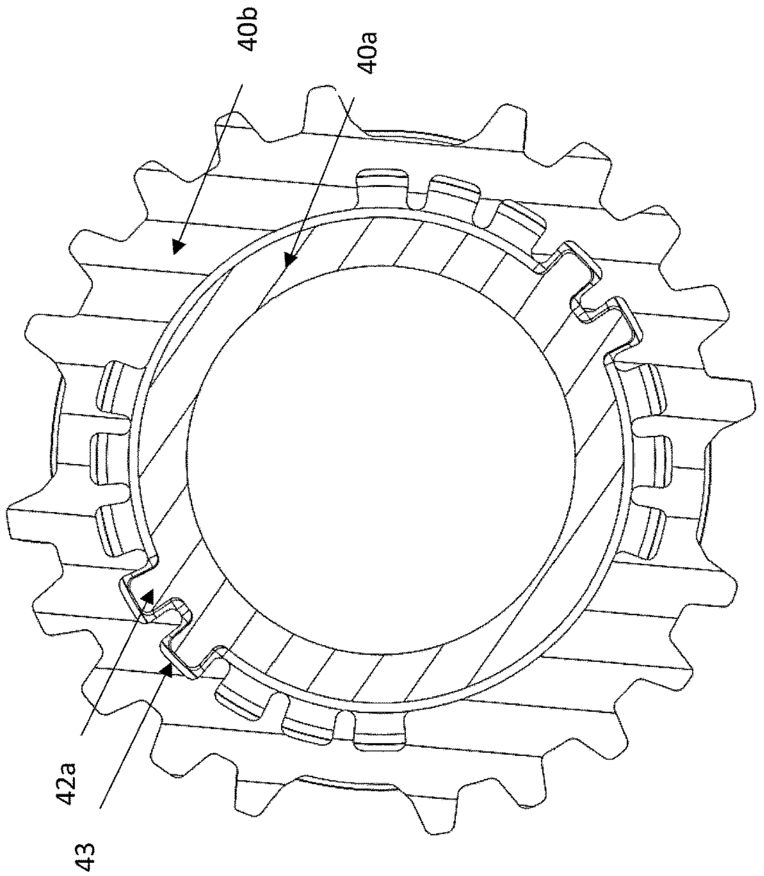
FIG. 10*d* shows yet another sectional view of the embodiment of FIGS. 10*a* and 10*b*.
Figure 10C:
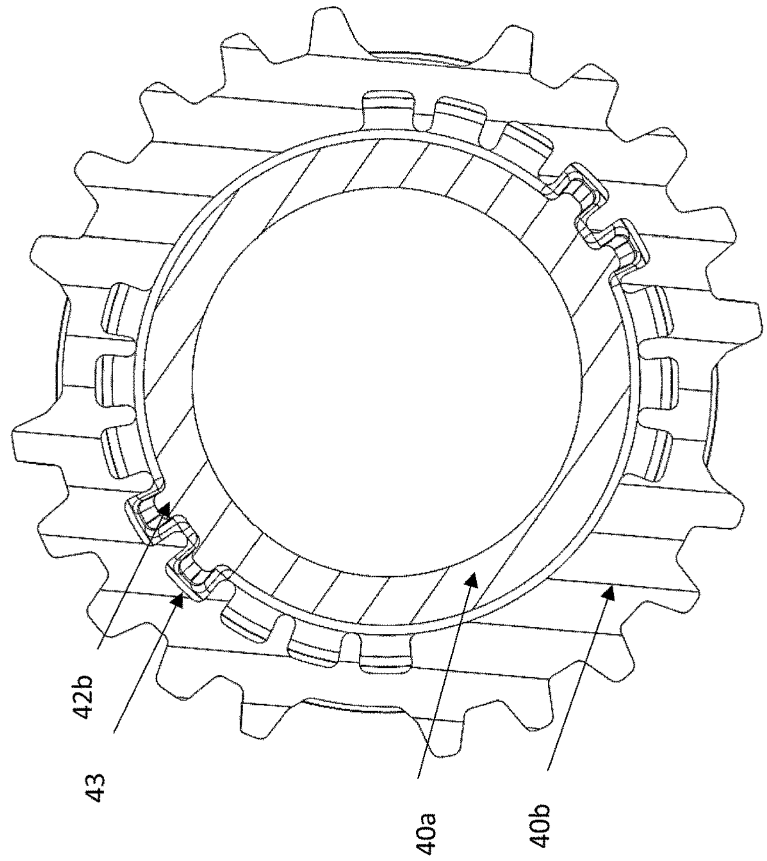
FIG. 10*c* shows a further sectional view of the embodiment of FIGS. 10*a* and 10*b;*
Figure 11:
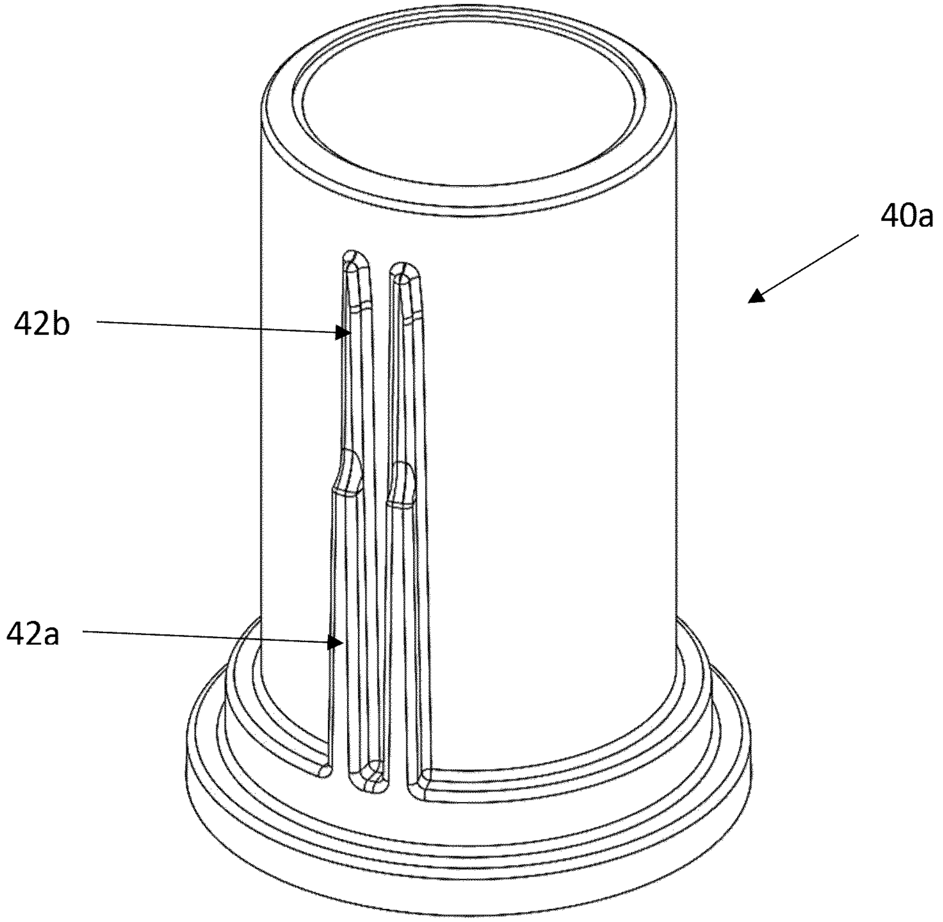
FIG. 11 shows a view of the surface of a first drive member according to any one of the embodiments of FIGS. 9*a*-10*d*.

FIG. 11 shows the outer surface of the first drive member 40*a* of the embodiments of FIGS. 9*a*, 9*b*, 9*c*, 9*d* and 10*a*, 10*b*, 10*c*, 10*d*. The outer surface comprises the first locking feature 42, wherein the first locking feature 42 is designed as at least one tooth or rib with a high area, i.e. a first locking portion 42*a*, and low area, i.e. a second locking portion 42*b*. The high area may protrude radially beyond the low area. The first locking feature may extend in the axial direction along the first drive member 40*a*. Specifically, it may be oriented axially. The first locking portion 42*a* is positioned in front of the second locking portion 42*b* in the axial distal direction. That is to say, the first locking portion may be arranged distally relative to the second locking portion. The first locking portion 42*a* is engaged with second locking feature 43 in the delivery state and the second locking portion 42*b* is engaged with second locking feature 43 in the stetting state.

As shown in the FIGS. 9*c* and 10*d*, the first locking portion 42*a* cannot rotate relative to the second locking feature 43, so no rotation of the first drive member 40*a* relative to the second drive member 40*b* is possible in the delivery state. This is achieved by choosing the height of the first locking portion 42*a* so that a recess formed by the second locking feature 43 is almost completely filled with the first locking portion 42*a*.

As shown in FIGS. 9*d* and 10*c*, the height of the second locking portion 42*b* is such that the recess of the second locking feature 43 is only partially filled by the second locking portion 42*b*. Thus, in the setting mode, the second locking portion 42*b* can slide over the second locking feature 43 with the help of an external force. Thus it is possible that the first drive member 40*a* can be moved in rotation relative to the second drive member 40*b* in the setting mode. However, due to the height of the second locking portion 42*b*, the second locking portion 42*b* preferably cannot slide over the second locking feature 43 without the aid of an external force. This prevents a setting that has already been made from being lost in the setting state. Furthermore, by sliding the second locking portion 42*b* over the second locking feature 43, an acoustic or haptic feedback can be created during the adjustment process.

In the embodiments of FIGS. 6*a*, 6*b*, 7*a*, 7*b*, 9*a*, 9*b*, 9*c*, 9*d*, 10*a*, 10*b*, 10*c*, and 10*d* the first locking feature 42 and the second locking feature 43 are designed such that when the first locking feature 42 is engaged with second locking feature 43, the first drive member 40*a* occupies one of several stable positions relative to the second drive member 40*b*. Preferably, these stable positions are defined by the respective relative distance of the immediately adjacent locking wedges to each other. The angular distance between the stable positions may be adjusted to the angle the user has to rotate a dose setting member to set the smallest dose which can be delivered by the drug delivery device. This dose may correspond to one unit increment. Moreover, the distance between the stable positions may be such that a movement of the first drive member 40*a* relative to the second drive member 40*b* from one of the stable positions to the next immediately adjacent stable position leads at most to an axial movement of the piston rod 30 corresponding to the axial movement of the piston rod 30 during the delivery of a dose of one unit increment. It is also conceivable to design the locking features 42 and 43 such that a movement of the first drive member 40*a* relative to the second drive member 40*b* from one of the stable positions to the next immediately adjacent stable position results in an axial movement of the piston rod 30 which would correspond to the axial movement of the piston rod 30 during the delivery of less than one unit increment, e.g. a half or a quarter unit increment.

In cases where the first locking feature 42 is not in engagement with the second locking feature 43 in the setting mode, such as in the embodiments of FIGS. 6*a* and 6*b*, the transition from the setting state to the delivery state should ensure that there is no jamming of the locking wedges of the locking features 42 and 43 which could impede axial displacement of the second drive member 40*b* in the distal direction. It may, therefore, be expedient for the first drive member 40*a* to be designed such that, after a rotational movement relative to the second drive member 40*b*, the first drive member 40*a* only comes to rest in a position relative to the second drive member 40*b* which corresponds to one of the stable positions, i.e. a position in which the locking wedges can interlock reliably. For example, the first drive member 40*a* can be rotated only stepwise relative to the second drive member 40*b*.

In the embodiments of the FIGS. 6*a*, 6*b*, 7*a*, 7*b*, 9*a*, 9*b*, 9*c*, 9*d*, 10*a*, 10*b*, 10*c*, and 10*d* the dose setting and drive mechanism comprises the dose setting member 60, which is moveable relative to the housing 10 in the setting state from an initial position to a dose set position in order to set a dose of drug. The dose setting member 60 is rotationally constrained with respect to the second drive member 40*b* in the delivery state and rotatable relative to the second drive member 40*b* in the setting state. The first drive member 40*a* may be rotationally constrained with respect to the dose setting member 60 and the second drive member 40*b* in the delivery state in the direction opposite to the delivery direction. Moreover, the first drive member 40*a* may be rotatable relative to the dose setting member 60 and the second drive member 40*b* in the delivery state in the delivery direction. The first drive member 40*a* may be rotatable relative to the dose setting member 60 and the second drive member 40*b* in the setting state in the delivery direction. Furthermore, the first drive member 40*a* may be rotatable relative to the dose setting member 60 and the second drive member 40*b* in the setting state in the delivery direction and in the direction opposite to the delivery direction.

The production of the drug delivery device, comprising one of the embodiments of FIGS. 6*a*, 6*b*, 7*a*, 7*b*, 9*a*, 9*b*, 9*c*, 9*d*, 10*a*, 10*b*, 10*c*, and 10*d* begins with the provision of the reservoir unit, which comprises the reservoir 100 containing the drug, wherein the bung is movably retained in the reservoir 100, and wherein the reservoir 100 being retained in the reservoir unit body 20, and the provision of the mechanism unit.

After that, the bung position of the bung relative to the reservoir unit body 20 is determined. In addition, a desired piston rod position of the piston rod 30 relative to the housing 10 is determined based on the determined bung position. The desired piston rod position is determined such that, if the mechanism unit and the reservoir unit are connected, the piston rod 30 and the bung are arranged at a predetermined distance relative to one another. Moreover, a particular displacement distance by which the piston rod 30 has to be displaced relative to the housing 10 in the distal direction to be in the desired piston rod position is determined. The predetermined distance between the piston rod 30 and the bung is the distance which, after assembly of the device, allows the exact dose set by the user to be delivered on first actuation of the drug delivery device.

Subsequently, in the setting state of the mechanism unit, the first drive member 40*a* is rotated relative to the second drive member 40*b* to displace the piston rod 30 relative to the housing by the particular displacement distance. Finally the reservoir unit and the mechanism unit are connected to one another.

However, it should be noted that the rotation of the first drive member 40*a* relative to the second drive member 40*b* to displace the piston rod 30 relative to the housing by the particular displacement distance may also be done after the reservoir unit and the mechanism unit are connected to one another and before the drug delivery device is fully assembled. As mentioned before, in this case, the first drive member 40*a* is accessible from the proximal end of the housing 10 via an opening which, after the proper piston rod position has been achieved, is closed by the button 70 during final assembly of the drug delivery device.

The terms “drug” or “medicament” are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient (“API”), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or “drug container” adapted for use with a drug delivery device. The drug container may be, e.g., a reservoir, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about-4° C. to about 4° C.). In some instances, the drug container may be or may include a dual-chamber reservoir configured to store two or more components of the pharmaceutical formulation to-be-administered (e.g., an API and a diluent, or two different drugs) separately, one in each chamber. In such instances, the two chambers of the dual-chamber reservoir may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des (B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des (B30) human insulin, B29-N-omega-carboxypentadecanoyl-gamma-L-glutamyl-des (B30) human insulin (insulin degludec, Tresiba®); B29-N—(N-lithocholyl-gamma-glutamyl)-des (B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091 March-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An examples of an oligonucleotide is, for example: mipomersen sodium (Kynamro®), a cholesterol-reducing antisense therapeutic for the treatment of familial hypercholesterolemia.

Examples of DPP4 inhibitors are Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present disclosure, which encompass such modifications and any and all equivalents thereof.

REFERENCE NUMERALS

10 housing (casing)
11*a, b* window
12 insert
13 sidewall
14 tube
15 arm
16 bottom wall
17 thread
18 spline teeth
19 ring-shaped second part
19*a* spline teeth
19*b* arm (spline)
190 arm (snap clip)
19*d* opening
20 reservoir unit body
30 piston rod
40 drive member
40*a* first drive member
40*b* second drive member
41 spline teeth
42 first locking feature
42*a* first locking portion
42*b* second locking portion
43 second locking feature
44 lock
45 thread guide
50 nut
60 dose setting member
60*a* dose setting member lower
60*b* dose setting member upper
70 button
80 dose selector
90 torsion spring
91 hook
100 reservoir
110 gauge element
120 clutch plate
130 clutch spring
140 bearing
I axis
D delivery direction

The invention claimed is:

1. A mechanism unit for a drug delivery device, the mechanism unit comprising:

a housing having a proximal end and a distal end;

a piston rod movable relative to the housing; and a dose setting and drive mechanism configured to perform a dose setting operation for setting a dose to be delivered and to perform a dose delivery operation for delivering the set dose by transferring a delivery force to the piston rod in order to drive the piston rod in a distal direction relative to the housing in the dose delivery operation, the dose setting and drive mechanism comprising a first drive member in mechanical cooperation with the piston rod to transfer the delivery force to the piston rod, the first drive member being axially secured and rotatable relative to the housing, wherein a rotation of the first drive member in a delivery direction relative to the housing results in a movement of the piston rod in the distal direction and a rotation in a direction opposite to the delivery direction results in a proximal movement of the piston rod, a second drive member arranged to be mechanically coupled to the first drive member to transfer the delivery force to the first drive member, and a clutch mechanism having at least a setting state and a delivery state, wherein, in the setting state, the second drive member is rotationally secured with respect to the housing at least against a rotation in the delivery direction, and wherein, in the delivery state, the second drive member is rotatable relative to the housing in the delivery direction, wherein, in the setting state, the first drive member is rotatable relative to the second drive member and the housing at least in the delivery direction, wherein, in the delivery state, the second drive member is rotationally locked to the first drive member at least against a rotation of the second drive member relative to the first drive member in the delivery direction, and wherein the second drive member is axially movable relative to the first drive member and the housing for switching between the setting state and the delivery state.

2. The mechanism unit according to claim 1, wherein the dose setting and drive mechanism comprises a dose setting member that is moveable relative to the housing in the setting state from an initial position to a dose set position in order to set a dose of drug.

3. The mechanism unit according to claim 1, wherein the mechanism unit is configured to be connected to a reservoir unit for assembling the drug delivery device, and wherein the first drive member is accessible from an exterior of the housing for manipulations such that, in the setting state, a position of the piston rod relative to the housing can be adjusted by rotation of the first drive member before or after the mechanism unit and the reservoir unit are connected.

4. The mechanism unit according to claim 1, wherein the second drive member is axially movable relative to the first drive member and the housing in the distal direction for switching between the setting state and the delivery state.

5. The mechanism unit according to claim 1, wherein the first drive member is engaged to the piston rod, and wherein the piston rod is engaged to the housing.

6. The mechanism unit according to claim 5, wherein the first drive member is threadedly engaged to the piston rod, and the piston rod is splined to the housing.

7. The mechanism unit according to claim 6, wherein the first drive member is rotatable relative to the piston rod.

8. The mechanism unit according to claim 5, wherein the first drive member is splined to the piston rod and the piston rod is threadedly engaged to the housing.

9. The mechanism unit according to claim 8, wherein the first drive member is rotatably secured to the piston rod.

10. The mechanism unit according to claim 1, wherein the first drive member is secured against proximal and distal movements relative to the housing.

11. The mechanism unit according to claim 1, wherein the first drive member comprises a first locking feature, and the second drive member comprises a second locking feature, and wherein, in the delivery state, the first locking feature is engaged with the second locking feature.

12. The mechanism unit according to claim 11, wherein, in the setting state, the first locking feature and the second locking feature are disengaged.

13. The mechanism unit according to claim 11, wherein, in the setting state, the first locking feature is engaged with the second locking feature.

14. The mechanism unit according to claim 11, wherein, the first locking feature and the second locking feature are configured such that the first locking feature is rotatable relative to the second locking feature in the delivery direction.

15. The mechanism unit according to claim 14, wherein the first locking feature and the second locking feature are configured such that the first locking feature is rotationally secured with respect to the second locking feature in the direction opposite to the delivery direction when the first locking feature is engaged with the second locking feature.

16. A drug delivery device comprising:
- a mechanism unit; and
- a reservoir unit comprising or being provided to retain a reservoir holding a drug,
- wherein the mechanism unit comprises
  - a housing having a proximal end and a distal end,
  - a piston rod movable relative to the housing, and
  - a dose setting and drive mechanism configured to perform a dose setting operation for setting a dose to be delivered and to perform a dose delivery operation for delivering the set dose by transferring a delivery force to the piston rod in order to drive the piston rod in a distal direction relative to the housing in the dose delivery operation, the dose setting and drive mechanism comprising
    - a first drive member in mechanical cooperation with the piston rod to transfer the delivery force to the piston rod, the first drive member being axially secured and rotatable relative to the housing, wherein a rotation of the first drive member in a delivery direction relative to the housing results in a movement of the piston rod in the distal direction and a rotation in a direction opposite to the delivery direction results in a proximal movement of the piston rod,
  - a second drive member arranged to be mechanically coupled to the first drive member to transfer the delivery force to the first drive member, and
  - a clutch mechanism having at least a setting state and a delivery state,
    - wherein, in the setting state, the second drive member is rotationally secured with respect to the housing at least against a rotation in the delivery direction, and wherein, in the delivery state, the second drive member is rotatable relative to the housing in the delivery direction,
    - wherein, in the setting state, the first drive member is rotatable relative to the second drive member and the housing at least in the delivery direction,
    - wherein, in the delivery state, the second drive member is rotationally locked to the first drive member at least against a rotation of the second drive member relative to the first drive member in the delivery direction, and
    - wherein the second drive member is axially movable relative to the first drive member and the housing for switching between the setting state and the delivery state.

17. The drug delivery device according to claim 16, wherein the first drive member is engaged to the piston rod, and wherein the piston rod is engaged to the housing.

18. The delivery device according to claim 17, wherein the first drive member is threadedly engaged to the piston rod and the piston rod is splined to the housing, or the first drive member is splined to the piston rod and the piston rod is threadedly engaged to the housing.

19. A method for dispensing a drug, the method comprising:
- providing a drug delivery device comprising
  - a reservoir unit comprising or being provided to retain a reservoir holding a drug,
  - a mechanism unit comprising:
    - a housing having a proximal end and a distal end,
    - a piston rod movable relative to the housing, and
    - a dose setting and drive mechanism configured to perform a dose setting operation for setting a dose to be delivered and to perform a dose delivery operation for delivering the set dose by transferring a delivery force to the piston rod in order to drive the piston rod in a distal direction relative to the housing in the dose delivery operation, the dose setting and drive mechanism comprising
      - a first drive member in mechanical cooperation with the piston rod to transfer the delivery force to the piston rod, the first drive member being axially secured and rotatable relative to the housing, wherein a rotation of the first drive member in a delivery direction relative to the housing results in a movement of the piston rod in the distal direction and a rotation in a direction opposite to the delivery direction results in a proximal movement of the piston rod,
      - a second drive member arranged to be mechanically coupled to the first drive member to transfer the delivery force to the first drive member, a clutch mechanism having at least a setting state and a delivery state, and a button, wherein, in the setting state, the second drive member is rotationally secured with respect to the housing at least against a rotation in the delivery direction, and wherein, in the delivery state, the second drive member is rotatable relative to the housing in the delivery direction, wherein, in the setting state, the first drive member is rotatable relative to the second drive member and the housing at least in the delivery direction, wherein, in the delivery state, the second drive member is rotationally locked to the first drive member at least against a rotation of the second drive member relative to the first drive member in the delivery direction, and wherein the second drive member is axially movable relative to the first drive member and the housing for switching between the setting state and the delivery state; and with the dose setting and drive mechanism in a state in which a dose of the drug has been selected, activating the dose setting and drive mechanism to commence delivery of the dose, wherein delivery of the dose is initiated by depressing the button axially in the distal direction.

* * * * *